(12) United States Patent
Valaskovic et al.

(10) Patent No.: US 7,681,926 B2
(45) Date of Patent: Mar. 23, 2010

(54) METHOD AND APPARATUS FOR CONNECTING SMALL DIAMETER TUBING

(75) Inventors: Gary A. Valaskovic, Cambridge, MA (US); Lee R. Sawdey, Merrimack, NH (US); James P. Murphy, Franklin, MA (US)

(73) Assignee: New Objective, Inc., Woburn, MA (US)

( * ) Notice: Subject to any disclaimer, the term of this patent is extended or adjusted under 35 U.S.C. 154(b) by 677 days.

(21) Appl. No.: 11/564,002

(22) Filed: Nov. 28, 2006

(65) Prior Publication Data

US 2007/0164562 A1   Jul. 19, 2007

Related U.S. Application Data

(63) Continuation-in-part of application No. PCT/EP2005/018944, filed on May 27, 2005.

(60) Provisional application No. 60/575,249, filed on May 28, 2004.

(51) Int. Cl.
*F16L 21/02* (2006.01)

(52) U.S. Cl. .................. 285/342; 285/343; 285/353; 285/93; 285/152.1; 285/124.5

(58) Field of Classification Search ............ 285/342, 285/343, 353, 249, 93, 149.1, 152.1, 124.2, 285/124.4, 124.5
See application file for complete search history.

(56) References Cited

U.S. PATENT DOCUMENTS

| | | | | | |
|---|---|---|---|---|---|
| 1,779,220 | A | * | 10/1930 | Strandell | 285/342 |
| 2,624,308 | A | * | 1/1953 | Wittlin | 116/276 |
| 3,233,920 | A | * | 2/1966 | Ammann | 285/54 |
| 3,880,452 | A | | 4/1975 | Fields | |
| 4,281,679 | A | * | 8/1981 | Stearns | 137/515.5 |
| 4,394,263 | A | * | 7/1983 | Dosch et al. | 210/198.2 |
| 4,529,230 | A | * | 7/1985 | Fatula, Jr. | 285/341 |
| 4,776,618 | A | * | 10/1988 | Barree | 285/341 |
| 4,787,656 | A | * | 11/1988 | Ryder | 285/148.23 |
| 4,991,883 | A | * | 2/1991 | Worden | 285/334.4 |
| 5,163,722 | A | * | 11/1992 | Worden | 285/375 |
| 5,234,235 | A | * | 8/1993 | Worden | 285/334.4 |

(Continued)

FOREIGN PATENT DOCUMENTS

EP        0706047        4/1996

(Continued)

OTHER PUBLICATIONS

Anal. Chem., vol. 67, p. 4549-4556, 1995.

(Continued)

*Primary Examiner*—David E Bochna
(74) *Attorney, Agent, or Firm*—Norris McLaughlin & Marcus PA

(57) ABSTRACT

A union for coupling two or more segments of tubing or optical fiber, having an elastomeric core with two or more tubular sections encased in a through bore of a union body, the ends of the union body bore having compression nuts having through bores for insertion of segments of tubing or optical fiber to be coupled, which, tubular sections, when compressed by the compression nuts, deform radially inwardly to hold and seal the segments of tubing or optical fiber inserted therein.

30 Claims, 19 Drawing Sheets

U.S. PATENT DOCUMENTS

| | | | |
|---|---|---|---|
| 5,288,113 A | * | 2/1994 | Silvis et al. ............... 285/342 |
| 5,487,569 A | * | 1/1996 | Silvis et al. ............... 285/24 |
| 5,494,641 A | * | 2/1996 | Krstanovic ............... 422/103 |
| 5,587,582 A | | 12/1996 | Henion et al. |
| 6,056,331 A | * | 5/2000 | Benett et al. ............... 285/343 |
| 6,116,274 A | * | 9/2000 | Ehrlich ............... 137/559 |
| 6,193,286 B1 | * | 2/2001 | Jones et al. ............... 285/354 |
| 6,200,113 B1 | * | 3/2001 | Van Davelaar ............... 417/571 |
| 6,848,720 B2 | * | 2/2005 | Carns et al. ............... 285/123.15 |
| 7,311,882 B1 | * | 12/2007 | Renzi ............... 422/103 |
| 7,338,088 B2 | * | 3/2008 | Salven et al. ............... 285/124.3 |

FOREIGN PATENT DOCUMENTS

| WO | WO 01/32245 | 5/2001 |
|---|---|---|

OTHER PUBLICATIONS

Rapid Comm. Mass Spectrom., vol. 11, p. 307-315, 1997.
Rapid. Commun. Mass Spectrom., vol. 13, p. 612-619, 1999.
Rapid Commun. Mass Spectrom., vol. 12, p. 1187-1191, 1998.
Rapid Commun. Mass Spectrom., vol. 13, p. 1-7, 1999.

* cited by examiner

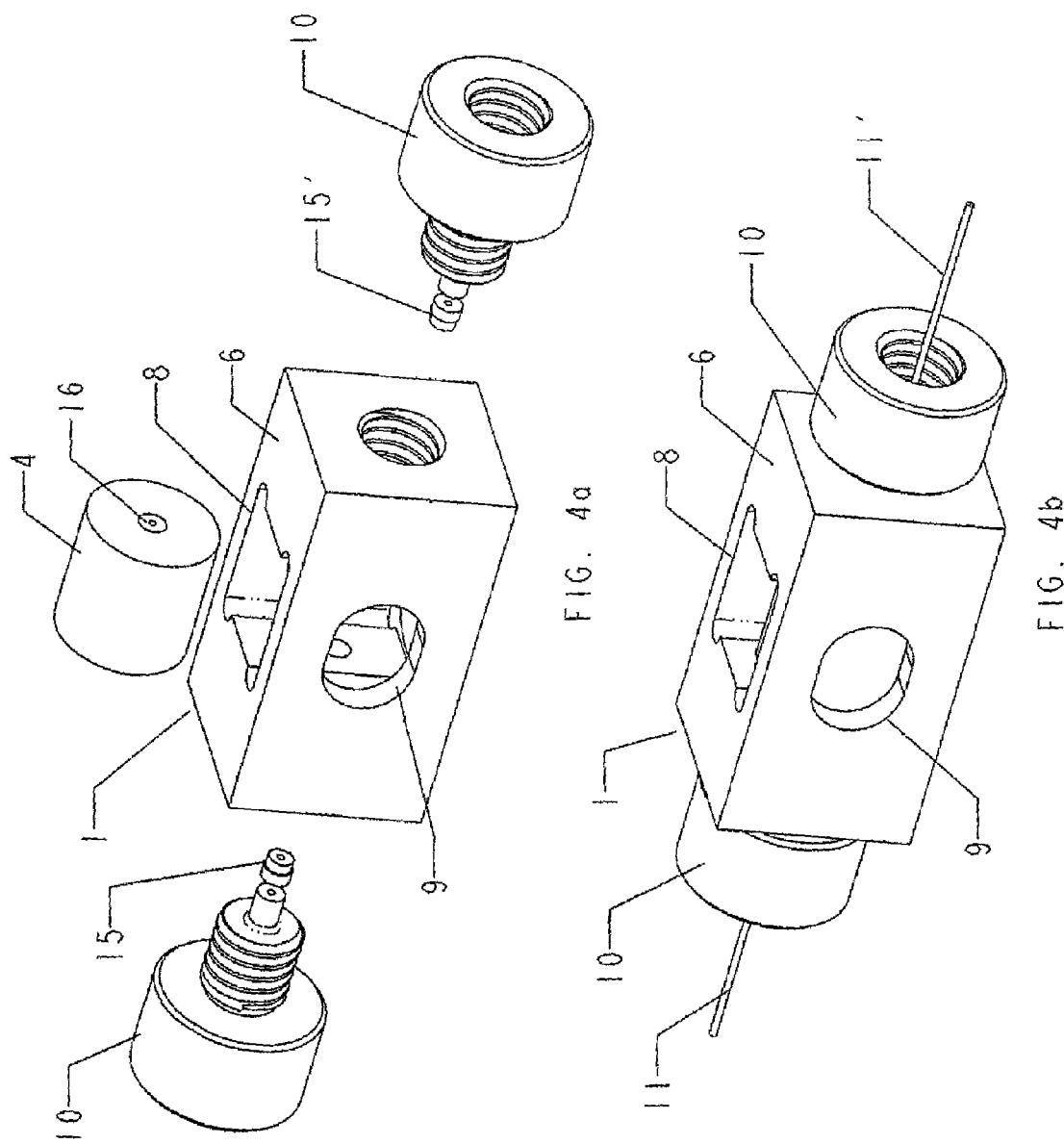

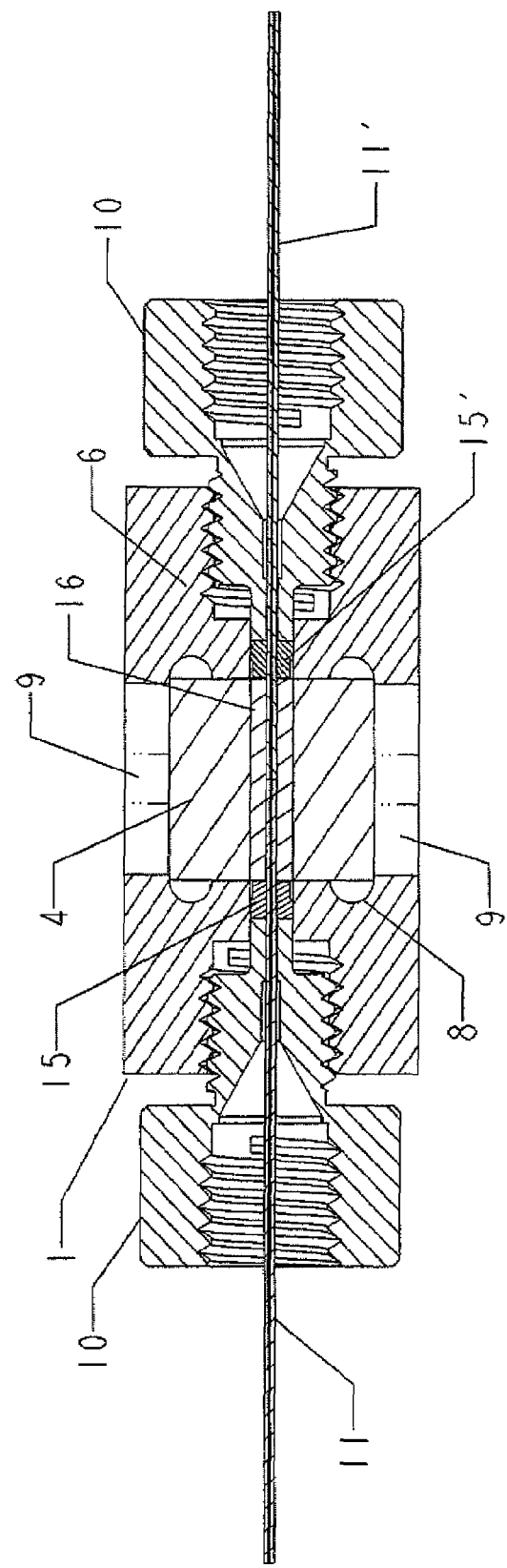

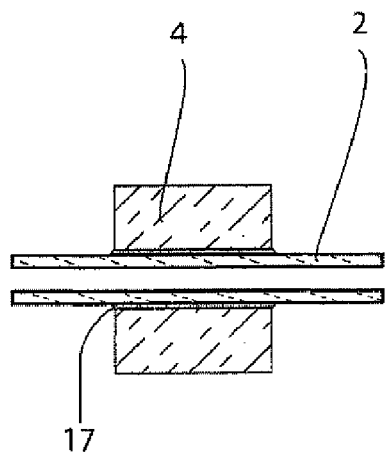
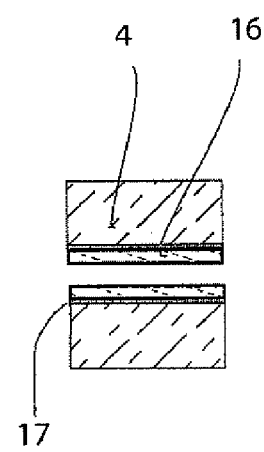
FIG. 5a
FIG. 5b
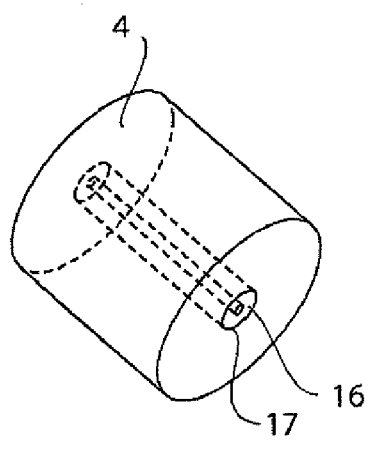
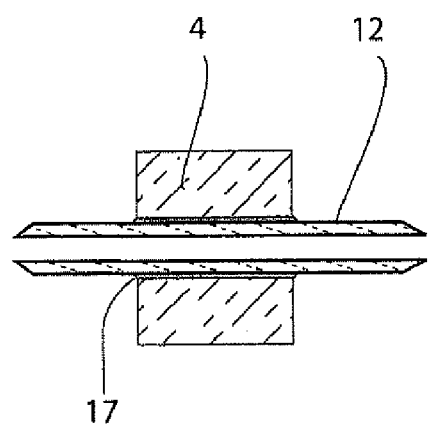
FIG. 5c
FIG. 6

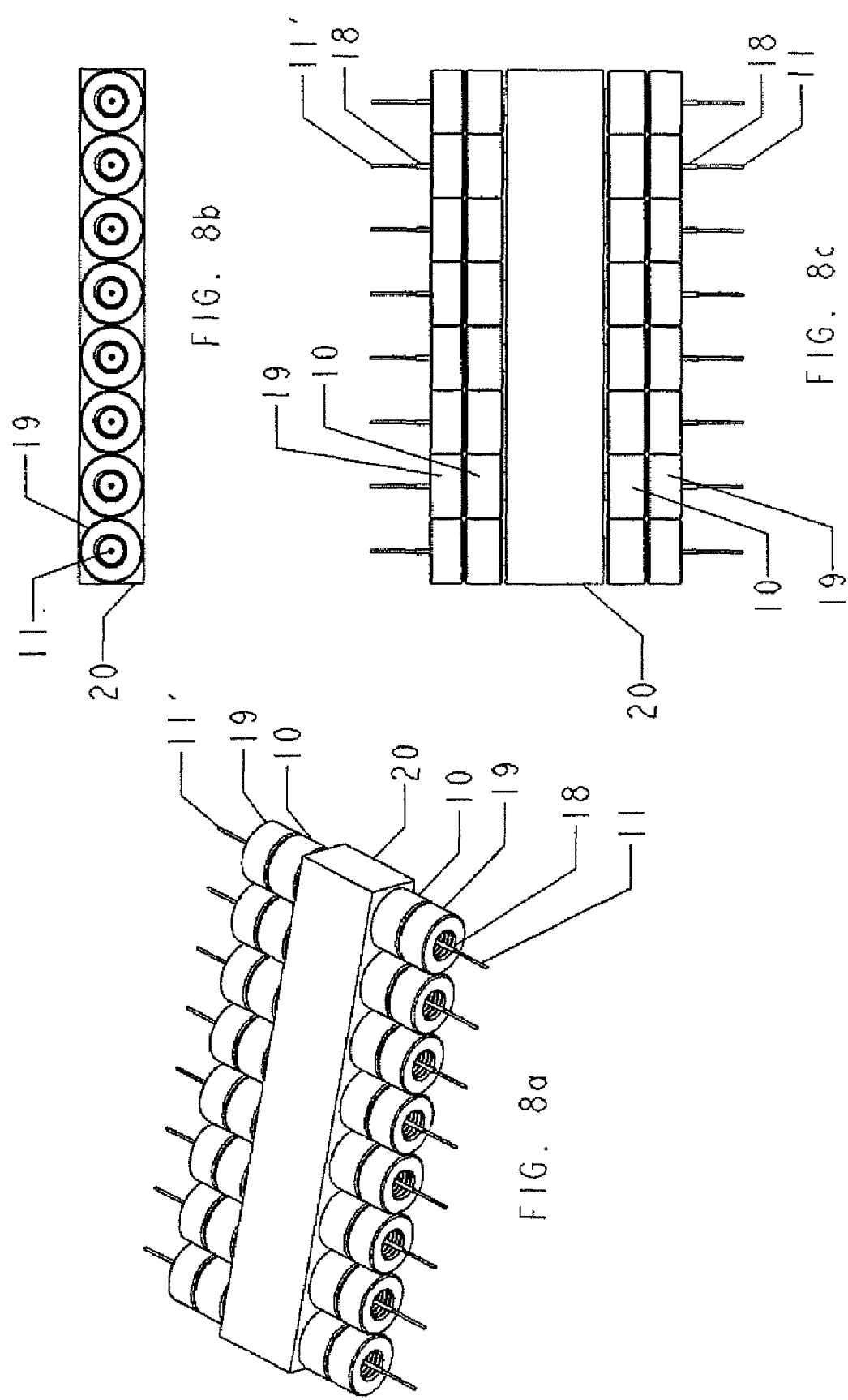

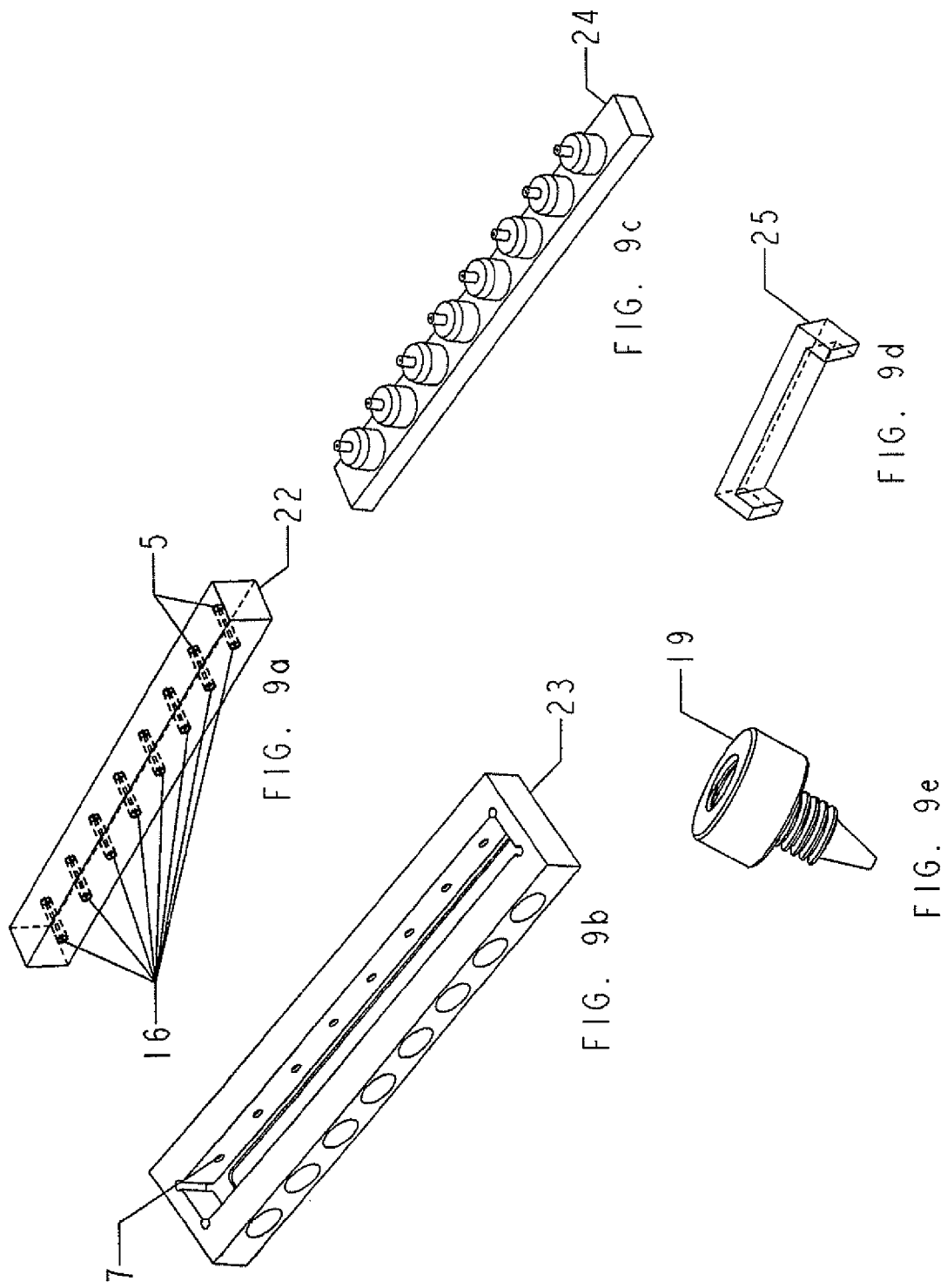

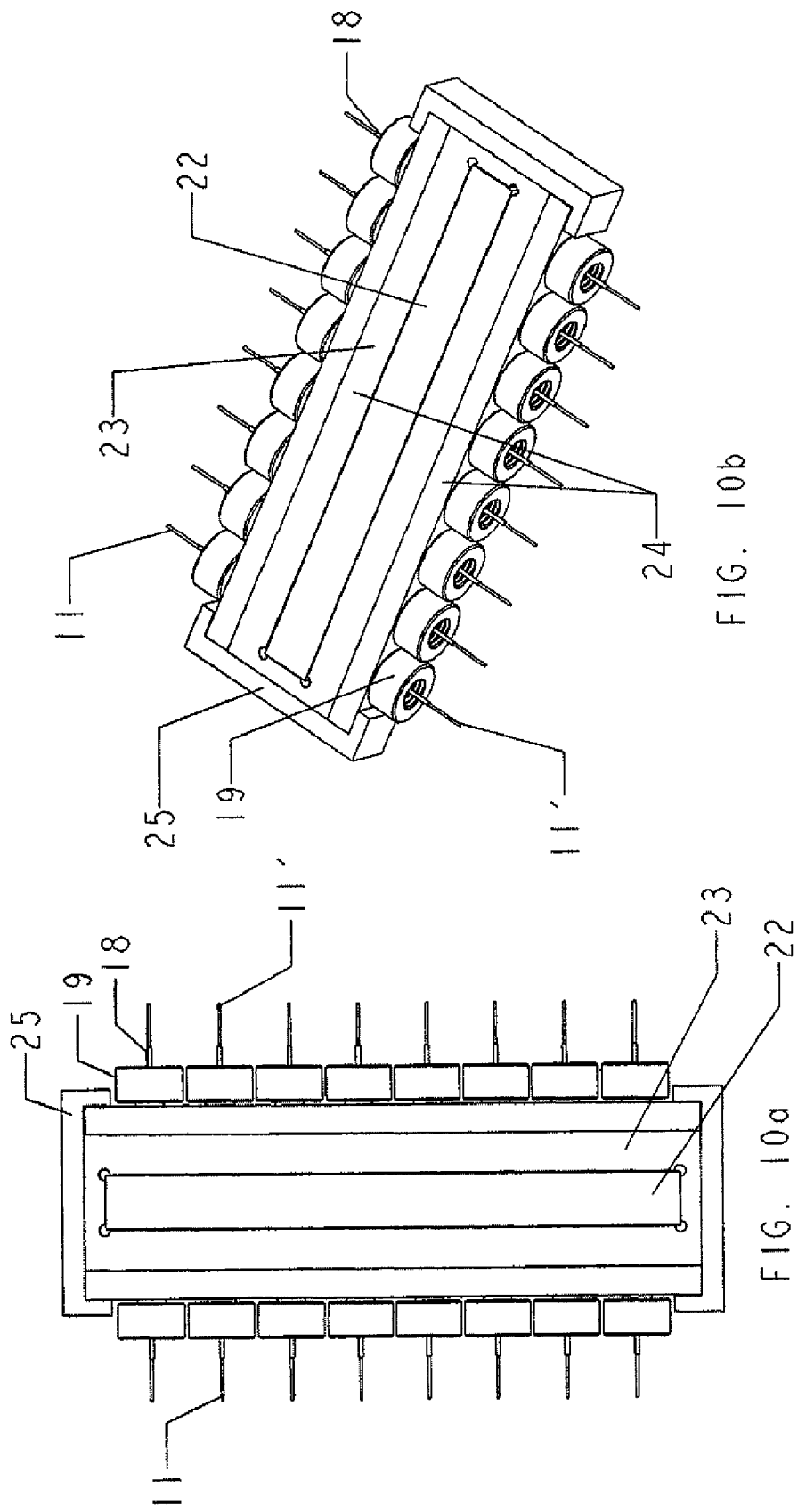

I.D. of elastomer is reduced to O.D. of Tubing

ID of elastomer is reduced to OD of Tubing

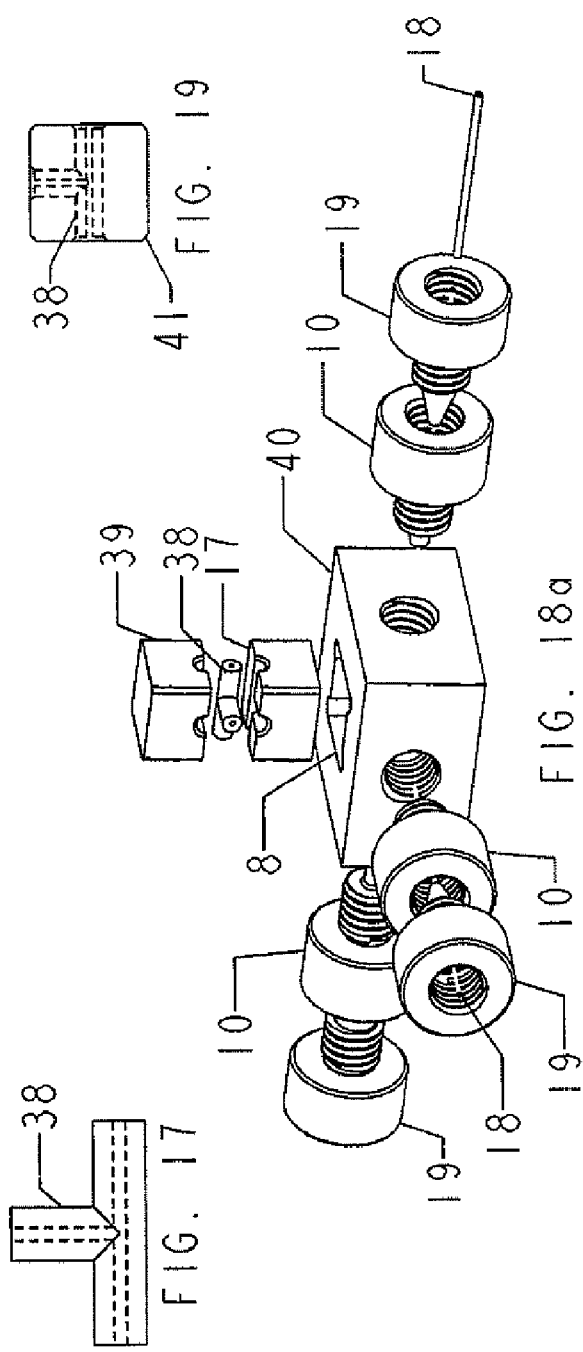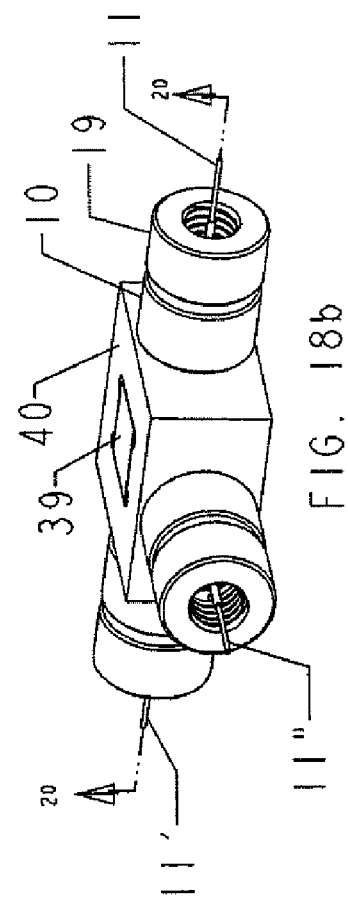

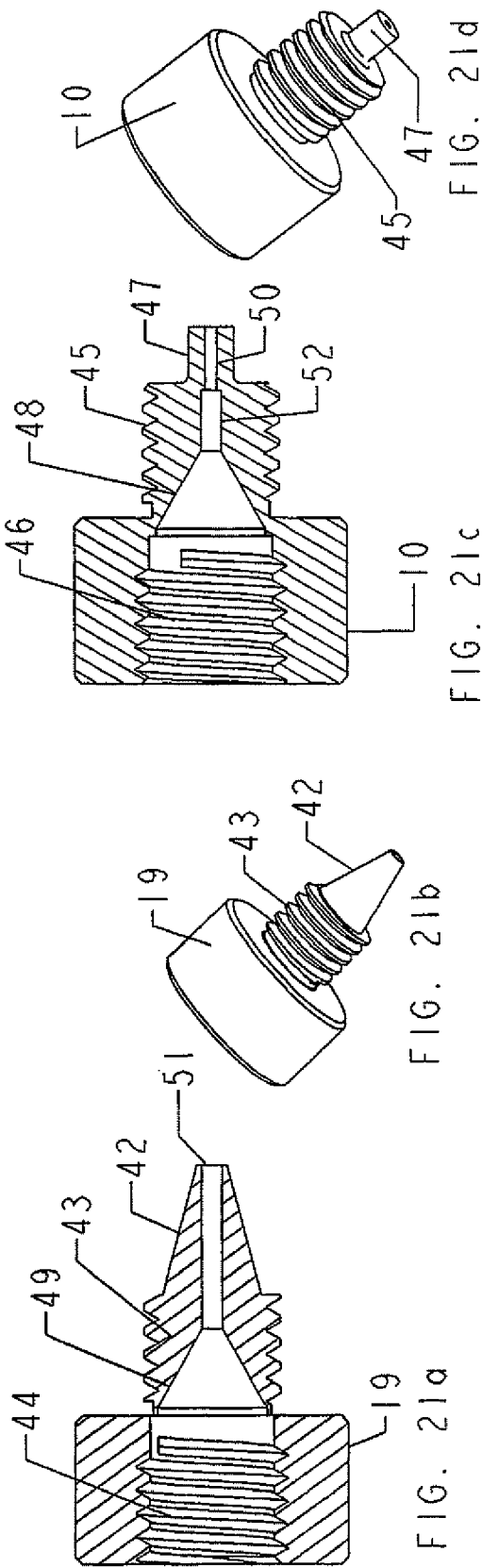

METHOD AND APPARATUS FOR CONNECTING SMALL DIAMETER TUBING

This application is a Continuation-In-Part of International Application Number PCT/EP2005/018944, filed on 27 May 2005, which claims the benefit of U.S. Provisional Application Ser. No. 60/575,249, filed on 28 May 2004, now pending.

This invention pertains to a method and apparatus, referred to as a union, whereby two or more segments of tubing, preferably small-diameter tubing or optical fiber, having a concentric inner bore or optical core, referred to hereinafter as "capillary tubing", may be efficiently connected. The connection provides for the coupling of the inside bore or core of each segment in a manner by which all extra-tubing volume within said connection is eliminated, referred to as a "zero dead-volume connection". Furthermore, a preferred embodiment provides an optically clear view of the connection. Thus, a user can immediately verify that the union and segments are properly assembled. Any significant gap or obstruction between the segments will be visible either by the unaided eye or through optical magnification with a lens or lens system. Such connections may even be monitored remotely with an electronic, analog or digital, opto-electronic monitoring system.

A principal utility of the invention is for the connection of two pieces of tubing to be used in chemical analysis by means of separation by either chromatographic or electrophoretic means. Liquid chromatography (LC), capillary electrophoresis, (CE) and gas chromatography (GC), and especially LC, CE or GC with chemical detection by mass spectrometry (MS) are especially benefited by this invention. For example, for use with LC-MS or CE-MS, one end of the outlet capillary tube may be a tapered hollow needle utilized as a source of ionized droplets that enter the mass spectrometer.

BACKGROUND OF THE INVENTION

Unions for the connection of tubing typically fall into one of two categories, those for high-pressure and those for low-pressure. High-pressure unions typically use either one or more tapered ferrules that fit around the outside diameter (OD) of the tubing. The bore of the union is shaped to accept both the OD of the tubing and a mating taper to that of the ferrule. A nut, which has a thread mating with that on the body of the union, which is in contact with the ferrule or ferrules, is tightened to provide compression of the ferrule into the body of the union. In this manner, the ferrule forms a liquid- and gas-tight seal between the outer surface of the tubing and the inner surface of the union. This type of union and mating action is typically referred to as frusto-conical compression. There are numerous examples of this frusto-conical compression in the prior art. Fields (U.S. Pat. No. 3,880,452), for example, with improvements by Worden (U.S. Pat. Nos. 4,991,883; 5,163,722; 5,234,235). Henion, Sheppard, Wachs (U.S. Pat. No. 5,587,582) utilized the frusto-conical approach substituting a "tee" junction for the union so that three pieces of tubing could be connected. Fatula (U.S. Pat. No. 4,529,230) simplified and improved this approach by reversing the direction of the taper and combined the two ferrules into a single unit, thus reducing the number of sealing surfaces from three to two. Jones, Porter, Kelly (U.S. Pat. No. 6,193,286) utilized spring loaded tension to push the tubing into the union coupling body in an attempt to ensure that the tubing is fully seated for frusto-conical compression. Davis, Stahl, Hefta, and Lee (Anal. Chem., Vol 67, p 4549-4556, 1995) and Bateman, White, and Thibault (Rapid Comm. Mass Spectrom., Vol 11, p. 307-315, 1997) summarize the use of frusto-conical high pressure couplings with capillary LC.

Low-pressure connections with small diameter capillary tubing are commonly made using a short segment of elastomeric tubing such as Teflon®, Teflon®-PFA, or KalRez® perfluoroelastomer as a coupling sleeve or union. The inside diameter (ID) of the elastomer tubing is chosen to be slightly smaller than the OD of the capillary tubing being connected. The two pieces of capillary tubing to be joined are press fit into respective ends of the elastomeric sleeve until their ends make direct contact for a butt connection. The interference fit between the ID of the sleeve and OD of the tubing results in strong friction between the coupling sleeve and the capillary tubing; holding the tubing in place. Various examples of this type of simple one-piece union appear in the literature: e.g. Gucek, Vreeken, Verheij (Rapid. Commun. Mass Spectrom., Vol 13, p. 612-619, 1999); Guzman (LC-GC, Vol. 17, 1999); Alexander, Schultz, Poli (Rapid Commun. Mass Spectrom., Vol 12, p. 1187-1191, 1998); and Herring, Qin (Rapid Commun. Mass Spectrom., Vol 13, p. 1-7, 1999).

Lowe (U.S. Pat. No. 822,530) teaches an embodiment in which an elastomer tube within a coupling body is used to connect two pieces of tubing. A combination of axial and radial compression, provided by tapered sections within the coupling body, is applied to the elastomer forms a seal between the two pieces of tubing, Each method has disadvantages. The high-pressure fittings can be difficult to use and often have many parts to assemble. It is typically difficult to verify the integrity of the coupling, which often requires partial disassembly. To overcome this particular limitation, Worden's patents ('883, '722, '235) use a removable, central seating element and spring loaded ferrules designed so the proximal ends of connecting tubing make direct contact with the central seating element rather than each other. This design overcomes the assembly problem of a conventional frusto-conical union, however, a significant amount of swept volume is added to the connection. The two pieces of tubing fit into the seating element and are separated by the length of the seating element.

A significant limitation of the apparatus disclosed by Lowe (U.S. Pat. No. 822,530) is a mechanical design that is overly constrained in the axis of the connected tubes. The co-axial alignment of the tubes being joined is highly dependant on the coaxial alignment of bores in the coupling body to both the bore of the elastomer tube and the outside surface of the tubes being joined.

The low-pressure sleeve approach can be quite efficient and provides an easy to use one-piece, see-through design. Use at high pressures (e.g. greater than 100 to 150 psi) is not routinely possible since the sleeve expands and distorts under pressure and the assembly does not hold together. Therefore, there is a need for an improved methodology and hardware for minimal volume capillary connections.

SUMMARY OF THE INVENTION

The union is comprised of a union body made up of a hard exterior shell, which may be cylindrical, having a through bore and a soft, elastomeric interior core within its through bore. The elastomeric core also has a through bore, preferably concentric with the through bore of the union body, giving it an ID that is smaller than the ID of the through bore of the union body. The purpose of the elastomeric core is to provide a deformable through bore, in which the ID is dependant upon the amount of pressure applied to the ends by compression elements, such as compression or tightening nuts, attached to the union body. Where tightening nuts are used as the compression elements, the nuts and the ends of the union body have complementary threads. These threads can be internal or external threads with respect to the union body to engage the tightening nuts with the union body. Tightening the nuts threads them to bear upon the ends of the elastomeric core, which imparts a compressive force upon the elastomeric core. The bore of the union housing prevents the elastomeric core from deforming radially outwardly, and it therefore deforms radially inwardly, under the compressive force, to seal and hold the segments of capillary tubing inserted therein. A critical feature of the design of the ferrules which compress the elastomer is that they have a through bore of sufficiently large diameter so as not to interfere with the alignment of the tubes being connected.

In a further embodiment of the invention, the union body is adapted for use with a union housing. A union housing for this use is configured to accept the union body as a cartridge, forming a cartridge-in-holder system. The union housing is provided with a first through bore, creating two open inlets. Each inlet end is optionally threaded internally for a portion of its length, to accommodate compression elements, such as tightening nuts. Optionally, an external thread can be on the outer surface of the union housing, concentric with the respective inlets. Optionally there are alternative forms of generating the compression within the core. Alternative embodiments include the use of springs, magnets, lever arms, piezoelectric materials, and hydraulics. The union housing has a shaped slot or recess, which is substantially orthogonal to the through bore, having a depth sufficient to penetrate the through bore. The slot is shaped to enable the union body to be readily removed, and replaced, from the union housing. The housing also preferably includes window cut-out(s), optionally provided with observation or magnifying lenses, through which the interior may be observed.

The union body in this case has a geometry and dimensions which enable it to fit within the slot or recess of the union housing, and does not require threaded ends, as the threaded ends of the union housing can be used to engage the compression elements. Most preferably the union body has both a cross-sectional geometry and outer dimensions which allow it to float freely within the union housing. The amount of float is, at a minimum, equal to one half the outer diameter of the tubes being joined. When the elastomer core is compressed and the inner diameter is reduced the union body will than come into alignment with the outer surface of the tubes being joined. This creates a connection in which the elastomer is self-aligning to the outer surfaces of the tubing being joined. The floating insert avoids the undesirable condition of excess mechanical constraint, ensuring co-axial alignment of the tubes and eliminates the need for parts manufactured to extremely high tolerance.

A further embodiment of the invention relates to a method of joining two or more segments of tubing or optical fiber using the union described herein.

A still further embodiment of the invention relates to a method of inspecting or monitoring the junction of two or more segments of tubing utilizing a union as described herein.

BRIEF DESCRIPTION OF THE DRAWINGS

FIG. 4a is an exploded view of a union having a housing and cylindrically shaped, free floating, union body.

FIG. 4b illustrates the union body of FIG. 4a as used to join two sections of tubing.

FIG. 4c is a cross-sectional view of the union of FIG. 4b.

FIG. 5a illustrates a preferred embodiment of a union body as a cartridge insert fabricated from a hard cylindrical shell, an elastomeric inner core extending beyond the ends of the union body bore, and an optional chemical bonding agent between the elastomeric core and union body bore.

FIG. 5b. Illustrates an embodiment similar to that as FIG. 5a, except that the ends of the elastomeric inner core terminate flush with the ends of the bore of the union body.

FIG. 5c is an isometric representation of the union body of FIG. 5b.

FIG. 6 illustrates an embodiment similar to that of FIG. 5a, but with the ends of the inner core suitably tapered for use with the ferrules of FIG. 4.

FIG. 8a illustrates a composite integral union body having a linear array of multiple individual unions, each having an individual bore and core (not shown), primary compression nut and secondary compression nut.

FIG. 8b is a side view of the integral union body of FIG. 8a.

FIG. 8c is a top view of the integral union body of FIG. 8a.

FIG. 9a illustrates a union body as a composite cartridge insert having a linear array of multiple bores and cores, configured for insertion into a complementary housing.

FIG. 9b illustrates a housing for the union body of FIG. 9a

FIG. 9c illustrates a plate having a series of compression elements, substituting for the compression nuts, which engages with the housing of FIG. 9b.

FIG. 9d illustrates a clamp used to hold the union body of FIG. 9a, the housing of FIG. 9b and two compression nut plates of FIG. 9c together to form a union.

FIG. 9e illustrates a secondary compression nut, with integral tapered ferrule, which can be used with the tightening nuts (primary nuts) of FIG. 9c to further secure tube or optical fiber segments being joined by the union.

FIG. 10a is a top view of the multi-port union formed of the union body of FIG. 9a, the housing of FIG. 9b and the clamps of FIG. 9d.

FIG. 10b is an isometric view of the multi-port union of FIG. 10a

FIG. 17 illustrates a "T" shaped elastomeric core.

FIG. 18a. is an exploded diagram of a union configured for use with the "T" shaped elastomeric core of FIG. 17, with a two-part, three-port union body and three-port union housing, primary compression nuts and secondary compression nuts.

FIG. 18b is an isometric view of the union of FIG. 18a, used to join three sections of tubing.

FIG. 19. illustrates a molded composite union body with a formed-in-place "T" shaped elastomeric core.

FIG. 21a is a cross-sectional view of a secondary compression nut with integral tapered ferrule.

FIG. 21b is an isometric representation of the secondary compression nut of FIG. 21a FIG. 21c is a cross-sectional view of a primary compression nut with a flat ended cylindrical protrusion.

FIG. 21d is an isometric representation of the primary compression nut of FIG. 21d.

FIG. 21e illustrates the mating of a secondary compression nut with a primary compression nut.

DETAILED DESCRIPTION

Figure 1:
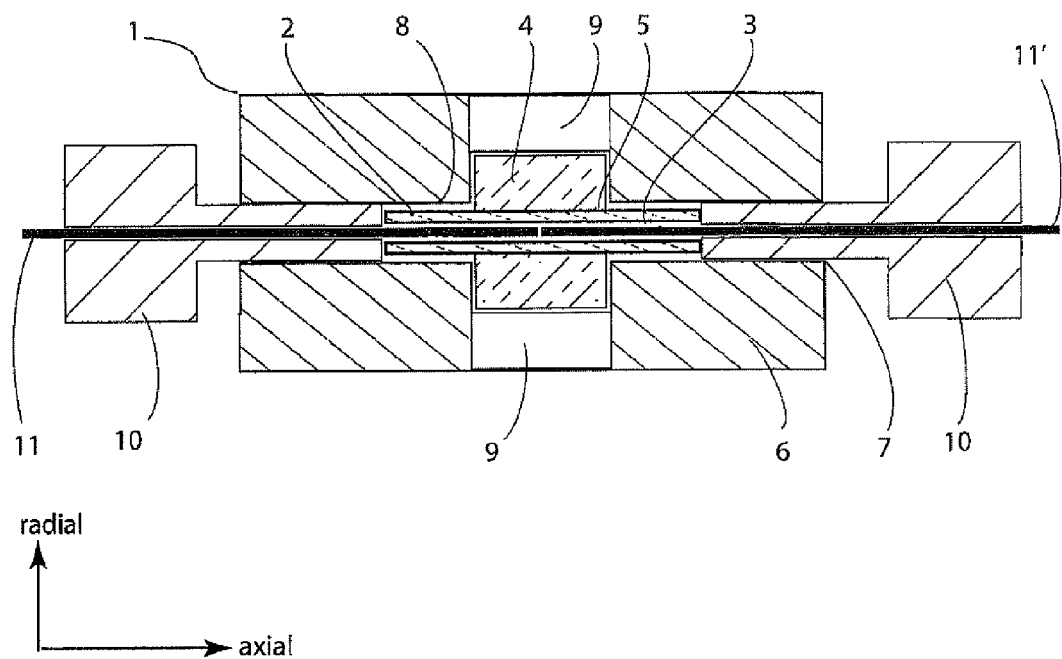
FIG. 1 is a schematic (cross section view) of one preferred embodiment of the invention. Here the proximal ends of the tightening nuts bear directly on the insert core as compression elements. The arrows define the axial and radial axis.

In accordance with the invention, there is provided a union for coupling two or more segments of tubing or optical fiber, comprising:
a) an elastomeric core having one or more linear or branched tubular sections, each having an internal bore, which, when more than one tubular section is present, is in fluid or optical communication with the internal bores of the other tubular sections,
b) a union body having a through bore for each of said one or more tubular sections, which girdles said tubular section or sections, the size and shape of said through bore or bores of said union body being complementary to the size and shape of the tubular core section girdled by each and the dimensions of said through bore or bores of said union body approximating but exceeding the outside diameter of the corresponding tubular core section, so as to substantially prevent radial expansion of said tubular core section or sections,
c) compression elements engagable with said union body to impart an axial compression upon said tubular elastomeric core section or sections,
whereby upon insertion of segments of tubing or optical fiber having an outside diameter which approximates but is less than the internal diameter of said bores of said section or sections of elastomeric core into said bores of said elastomeric core section or sections and axial compression of said elastomeric core section or sections by said compression elements in combination with the prevention of radial expansion of said elastomeric core section or sections by said bore or bores of said union body, an inward radial compression is imparted to said elastomeric core section or sections to sealingly engage said segments of said tubing or optical fiber.

In another aspect, the invention comprises a union for coupling two or more segments of tubing or optical fiber, comprising:
a) an elastomeric core having one or more linear or branched tubular sections, each having an internal bore, which, when more than one tubular section is present, is in fluid or optical communication with the internal bores of the other tubular sections,
b) a union body having a through bore for each of said one or more tubular sections, which girdles said tubular section or sections, the size and shape of said through bore or bores of said union body being complementary to the size and shape of the tubular core section girdled by each and the dimensions of said through bore or bores of said union body approximating but exceeding the outside diameter of the corresponding tubular core section, so as to substantially prevent outward radial expansion of said tubular core section or sections.

The union body is preferably a hard shell. The hard shell of the union body serves several purposes. The hard shell of which the union body is formed prevents the outside diameter of the elastomeric core from expanding in the radial direction; the elastomeric core's outside diameter (OD) is limited by the inside diameter (ID) of the through bore of the hard shell This concentrates the deformation of the core which results from the tightening of the compression elements, preferably compression fittings such as compression nuts (also referred to as "primary compression nuts"), to the collapse of the core's ID as pressure is applied from the outside by the nuts, essentially transforming the axial compression to a radial compression, as illustrated in FIGS. 11a, 11b, 12a and 12b. The hard shell assures that the elastomeric core is properly positioned and centered within the body of the union. This eliminates errors of concentricity, such as those which occur due to tolerance stack-up in multi-part or multi-sleeve frusto-conical systems. The single-piece elastomeric core assures that both pieces of tubing are in good concentric registration. If the shell and core materials are optically transparent, the assembly will be optically clear. Thus the integrity of the union may be verified and monitored.

The preferable geometry of the union body is cylindrical, although there are numerous other functional geometries possible. In this preferred embodiment, a housing having a slot with an opening larger than the OD of the union body may be matched with the union body. In this embodiment, the through bore of the housing should be concentric with the outer surface of the union body. The slot in the union body has dimensions of depth and/or width which allow for sufficient clearance of the union body within the union housing so that the union body may float freely within the plane that is perpendicular to the axis defined by the through bore of the tubing being connected. The amount of free motion within said plane is at a minimum equal to half the outer diameter of tubing being joined, and may be larger. This clearance provides for the self alignment of the union body elastomer core to the outer surface of the tubes being joined. The slot through the union housing may also be a through bore so that the union body may be inserted for two different directions opposite to each other, separated by 180 degrees. The elastomeric core should have an OD that equals or approximates but is slightly smaller than the inner diameter (ID) of the through bore of the union body. The elastomeric core also has a through bore that is concentric with its OD. The union body and elastomeric core are fabricated so that the two effectively become a single unit. That is, the outer surface of the core is in intimate physical or chemical contact with the inside surface of the through bore of the union body. Alternatively the elastomeric core and union body may be held together by chemical bonding with a third material (FIGS. 5a, 5b).

The union body may also be configured to work in a linear array by creating a single insert having a plurality of elastomeric core sections, such as the linear array (composite core) shown in FIGS. 8a-c or that shown in FIG. 10a-b. Thus when held in a suitably configured housing designed to accept multiple parallel connections (FIG. 9b), multiple connections may be made in parallel and in close proximity to each other. Matching plates, such as that shown in FIG. 9c, each comprising a series of compression nuts then complete the union. The compression element plates, union body and composite core can then be held in place by a clamp (FIG. 9d). The assembled multi-core union is shown in FIGS. 10a and 10b. This linear array may be extended to a two dimensional array by combining the herein described linear array in a stacked arrangement. In a further embodiment, the linear array embodiment may be extended in dimension so that the union body has multiple rows of through bores, each filled with an elastomer core. Compression plates (similar to that shown in FIG. 9c) having compression elements to match the spacing of the through bore array are placed on both sides of the union body. The entire composite array can be compressed simultaneously, by suitably compressing the plates in a fixture, such as a vise; or, by using screws to pull the plates together using complementary threaded and through bore holes in each plate.

In yet another linear array embodiment (FIGS. 8d-g), the union housing has multiple through bores with internal threads to accept multiple nuts and ferrules and multiple recesses to accept a cartridge union body and core insert in each array position, identical to the manner used in the single connection device. This embodiment allows for individual connections to be made in the array.

Most preferably the materials for the union body, core, and bonding agent are chosen to provide optical clarity in addition to other desirable physiochemical characteristics. The union body material should be harder than the core material, and resist structural deformation while the assembly is under load. As a result the core ID is deformed (reduced) to intimately contact the mating surfaces of the tubing being joined. The body remains for the most part undistorted, and limits the deformation of the outer surface of the core, deformation of the core's inner surface is therefore maximized. The core is preferably made from a material having a high degree of chemical inertness, since, in the absence of a perfect abutment of the two tubing sections, its inner surface is likely to come into contact with the fluid conducted by the tubing being connected.

Suitable materials for the union body material include optically clear, transparent materials such as: borosilicate glass; fused-silica; quartz; and hard, optically transparent or transmissive polymers such as Lexan® (polycarbonate), polymethylmethacrylate, Ultem® (polyetherimide), polyimide, Halar® (ethylenechlorotrifluoroethylene), Radel® A(polyethersulphone), Radel® R (polyphenylsulfone), Tefzel® (ethylene-tetrafuoroethylene), and Vivak® (PET-g, glycosilated polyester terephtalate). Suitable materials for the core include clear, flexible, inert elastomeric polymers and co-polymers: one or two-part silicones such as polydimethylsiloxane; Tygon® (polyvinylchloride); and fluoropolymers/co-polymers such as: Teflon® (polytetrafluoroethylene), Teflon® FEP (polyhexafluoropropylene-tetrafluoroethylene), Teflon® PFA (polyperfluoroalkoxyethylene), and Kel-F® (polychlorotrifluoroethylene).

Suitable fabrication methods for the union body include: (1) Two component injection molding of both the core and body components. (2) Injection molding of the body over a prefabricated core (such as that provided by a length of suitable elastomer tubing). (3) Casting a liquid polymer shell (body) over a prefabricated core. (4) Assembly of the composite from cut or machined sections of shell and core materials, using a chemical bonding agent to hold the assembly together (Such as cut lengths of extruded glass or polymer tubing for the body, and cut lengths of extruded FEP or similar elastomer tubing for the core).

For body fabrications utilizing chemical bonding between union body bore and elastomeric core, suitable bonding agents include single and two part (epoxy) adhesive systems. Particularly suitable are UV and heat curable polymers made for their optical clarity. Examples include mono and multi-functionalized acrylate/methacrylate liquid polymers and styrene/polyester liquid polymers containing a UV or thermally sensitive photo-initiator. Proprietary formulations of these adhesives from the Norland Optical Company or Summers Optical Company are particularly suitable. Conventional cyanoacrylate/methacrylate "super glue" adhesive formulations have also proven suitable.

If an extruded or molded fluoropolymer is used for the core material, it is preferable to chemically etch the outside surface of the material to improve the core's adhesion to the bonding agent. Suitable etching agents include the use of metallic sodium such as the commercially available formulation of sodium in naphthalene known as FluoroEtch® from the Acton Corporation. Fluorine molecules are stripped from the carbon backbone of the fluoropolymer during etching, promoting reactivity and adhesion of the carbon containing polymer backbone.

Suitable materials for the housing include hard, rigid materials that are sufficiently strong to resist deformation when the compression nuts are tightened to generate the pressure necessary to deform the core. That is the housing and compression elements, such as compression nut and ferrule components, must deform less than the elastomeric core when the compression nuts are tightened. The housing may preferably be made from metals such as steel, stainless steel, titanium, aluminum. Hard, rigid engineering plastic polymers are also suitable. Preferably suitable are polymers including PEEK® (polyether-ether ketone), Ultem® (polyetherimide), Delrin® (polyacetal), Nylon® (polyamide) and other polyamides and polyimides. The housing may be fabricated by conventional machining methods, plastic injection molding, metal injection molding, casting, and powder forming.

The union housing is preferably constructed with a window cut out, or preferably two opposing window cut outs, so that a glass or plastic observation or magnifying lens may be inserted to provide a direct or magnified view through the (transparent) union body and core to observe the connection at the center of the core and verify its integrity. When a magnification lens is used, the magnification is preferably 2× or more.

The window described herein for coupling verification may also be utilized in any number of optical detection schemes (UV absorbance, fluorescence, refractive index, etc.) known to those skilled in the art of chromatographic separation and detection. For example, the connection formed in the union, whether the union body is used with or without a housing, may be monitored with a visual system comprising a lens system and opto-electronic imaging device (charged-coupled device (CCD), complementary metal oxide semiconductor (CMOS), or similar) and microprocessor based computer imaging system. The microprocessor obtains an image from said imaging device and obtains quantitative information from said image. In one embodiment the imaging system contains a reference image of an acceptable connection to which the microprocessor compares the acquired image using a pattern matching algorithm. Such pattern matching uses the mathematical technique of cross-correlation, a method well known to those skilled in the art of two-dimensional mathematics and image processing. The pattern matching algorithm yields a result (a number) which is defined as the correlation coefficient, a quantitative indication of how well the reference and acquired images agree. When the correlation coefficient is greater than a previously established threshold level, the connection is determined to be acceptable. When the correlation coefficient is less than the threshold level, the connection is determined to be unacceptable.

In a second embodiment using machine vision, the quality of the connection is determined through the quantitative analysis of image morphology. In this embodiment, the ends of the two pieces of tubing are located though a edge-detection algorithm. The edge detection algorithm finds edges based on the contrast of the image, finding the location of large changes in image intensity over short distances. Such methods are well known to those skilled in the art of image processing, and are typically based on the two-dimensional mathematical derivative of the image. When the location of, and distance between, the edges are less than a previously established threshold value, the connection is determined to be acceptable. Indeed, when the two pieces of tubing are in contact, only a single edge is readily observed. When the distance between edges is greater than the threshold level, the connection is determined to be unacceptable.

In a further embodiment the imaging opto-electronic detector described above is replaced with a "non imaging" single element detector capable of measuring the light transmission through the union assembly.

In further embodiments, opto-electronic detection capable of yielding quantitative information about the separation distance between the two lengths of tubing being connected may be used as part of an automated feedback loop to control and maintain a given separation distance between the lengths of tubing. Particularly suitable for this purpose is the apparatus shown in FIG. 14 which yields an output voltage that is proportional to the gap between the lengths of tubing. The tubing being connected may be held by a suitable fixture that is in turn controlled by an electromechanical positioning system. Particularly suitable for this purpose are servo motor and stepper motor driven actuators, well known to those skilled in the art. The output voltage is fed to a negative feedback control circuit comprised of a so called proportional integrative derivative (PID) analog or digital circuit. This circuit compares the output voltage of the detector with a reference value and controls the electromechanical actuator to minimize the error between the detector output and reference value.

In addition to coupling two pieces of tubing or optical fibers, the composite cartridge assembly may also form other functional elements useful for handling of liquids and gases. For example, a filter system may be formed by one of two methods. (1) A porous material, such as a glass, polymer, or metal frit may be placed in-between the two sections of tubing prior to compression. (2) One of the lengths of connecting tubing may have a porous frit contained at or near its proximal end. In either case the porous frit permits the flow of liquid or gas, but substantially prevents the flow of particulate matter of a diameter near or larger than the frit's pore size. Said filter may also form the basis for use as slurry packing column hardware suitable for the fabrication of columns for use in gas or liquid chromatography.

The elastomeric core may also be fabricated from an electrically conductive material so that an electrical potential may be applied to the mobile phase being transferred from the first to second tube. This applied voltage may be suitable for use in capillary electrophoresis, capillary electrochromatography, and electrospray ionization for example. Suitable materials include electrically conductive elastomeric polymers. As is known to those skilled in the art of polymer formulation, conductive elastomeric polymer may be fabricated from the aforementioned elastomeric polymers by blending in a finely divided electrically conductive particulate material such as carbon, gold, platinum, silver or the like. In an alternative approach, a conductive polymer (such as polyaniline or iodine doped trans-polyacetylene) can be blended with the elastomer to impart electrical conductivity.

Alternatively, electrical conductivity can be imparted through the use of a core material fabricated from a polymer that permits conduction through ion mobility. Thus the core would be electrically conductive provided that the core is saturated with an aqueous or organic (e.g. methanol or acetonitrile) mobile phase containing conductive (solvated) ions such as sodium, potassium, ammonium, hydronium, acetate, or formate. Particularly suitable core materials include a cation selective material of poly-tetrafluoroethylensulfonate (Permepure Inc., Tom River N.Y.). Such cores enable electrical conductivity from the outside of the core to a mobile phase being transferred from the first to second tube when suitable ion containing liquids are being transferred.

Figure 7:
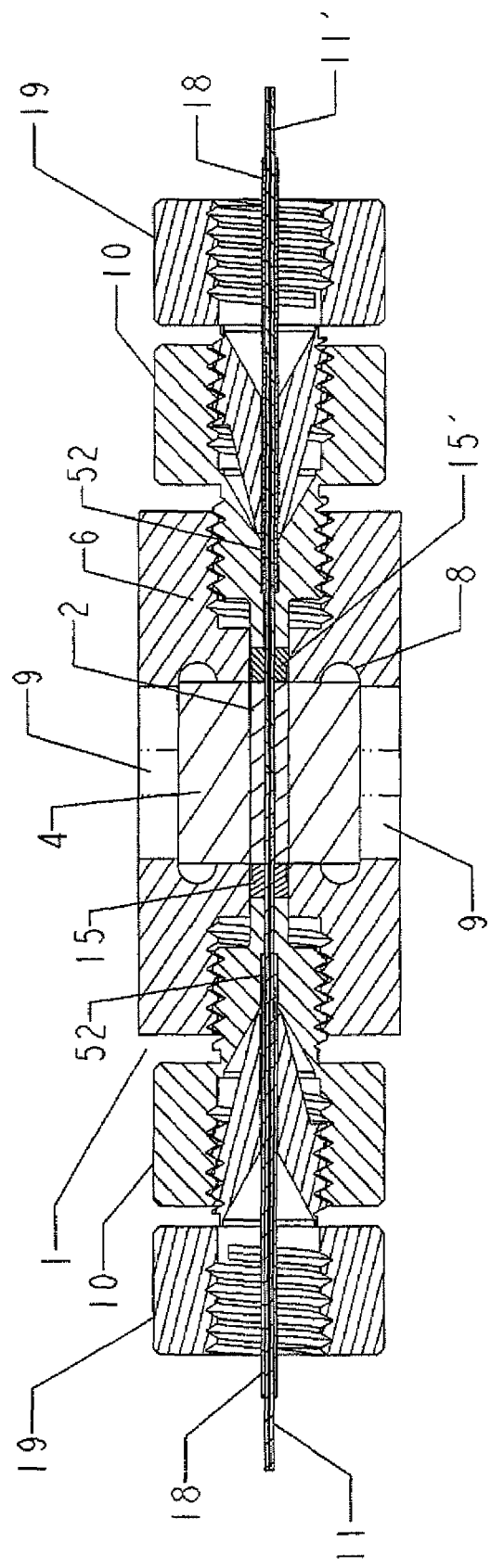
FIG. 7 illustrates the embodiment of FIG. 4c, with secondary compression nuts and polymeric sleeves for the secondary compression nuts added.

The frictional holding power between core and tubing may, in some cases, especially under very high pressure, be insufficient to maintain the two tubing segments in direct contact. The performance of the invention under such circumstances may be improved by the addition of (secondary) frusto-conical holding elements or secondary compression nuts to the assembly, as shown in FIG. 7. Preferably this additional, secondary, frusto-conical compression is provided by a ferrule and compression nut or compression nut with integral ferrule that mate into the distal end of each primary compression nut (FIG. 7). In such applications, the element which heretofore has been referred to as a "compression nut" is referred to as a "primary compression nut" and the additional nut is referred to as a "secondary compression nut". In the embodiment shown in FIG. 7, each primary compression nut has a distal end with an internal bore having a suitable internal taper and thread that mates with the secondary ferrule and complementary threaded secondary compression nut. Thus each end of the tubing being connected is held in place by a conventional frusto-conical sealing system positioned outboard of the composite union body. This second set of nut and ferrule, which is preferably in direct contact with each tubing segment, provides positive engagement with the tubing segments. When the liquid or gas being communicated through the tubing is pressurized the tubing holds firmly in place. The force generated by the contained liquid or gas, that may otherwise cause the two segments of tubing to be forced apart, is resisted by the greater holding force provided by the secondary ferrules. This is especially useful if the coefficient of friction between the core and tubing is low.

This particular embodiment may be preferably modified by the addition of polymer sleeves around the outer diameter of the tubing, as shown in FIG. 7, so that tubing of very small outer diameter (erg. less than 0.5 mm) may be firmly held. This embodiment may also be simplified by combining the secondary compression nut and ferrule into a single piece unit, as illustrated in FIGS. 21a and 21b (secondary compression nut with integral ferrule).

In a further embodiment, the union may be configured as a "T", "Cross" or "star" which would be especially useful as a manifold having 3, 4 or more ports. For this embodiment, a tee-, cross- or star shaped elastomeric core, as exemplified by the T-shaped core 38 of FIG. 17, may be prepared by any of several methods known to those skilled in the art, including but not limited to casting or molding. The core is then inserted into a multi-port union body, which is most simply done with a two-part union body 39 such as that shown in FIG. 18a, which can then be closed over the core and sealed by e.g. adhesive bonding or welding. The sealed multi-port union body is then inserted into a complementary recess in a similarly configured multi-port union housing 40, and primary compression nuts 10 and secondary compression nuts 19 inserted in the respective bores of the multi-port union body. The corresponding tubing or optical fiber sections are then inserted, as previously described, and the tightening nuts and secondary holding nuts tightened to form the seals and hold the tubing or optical fibers in place, as shown in FIG. 18b. Polymeric tubing sleeves 18 are optionally used to increase the holding power of the secondary compression nuts on the tube sections, as further discussed hereinafter.

Alternatively, the composite union body with tee-, cross- or star-shaped elastomeric core can be formed by casting or molding. The molded union body in such cases would include features that would allow the internal cavity to be filled with an elastomeric resin which would be cast or molded and cured in place, to form a composite insert 41 as shown in FIG. 19.

In yet a further embodiment, a three dimensional core, such as e.g. a spherically configured core with radially outward projecting core sections are used with an appropriately configured union body and optional housing. This embodiment is especially useful for mixing a plurality of fluids.

Figure 20:
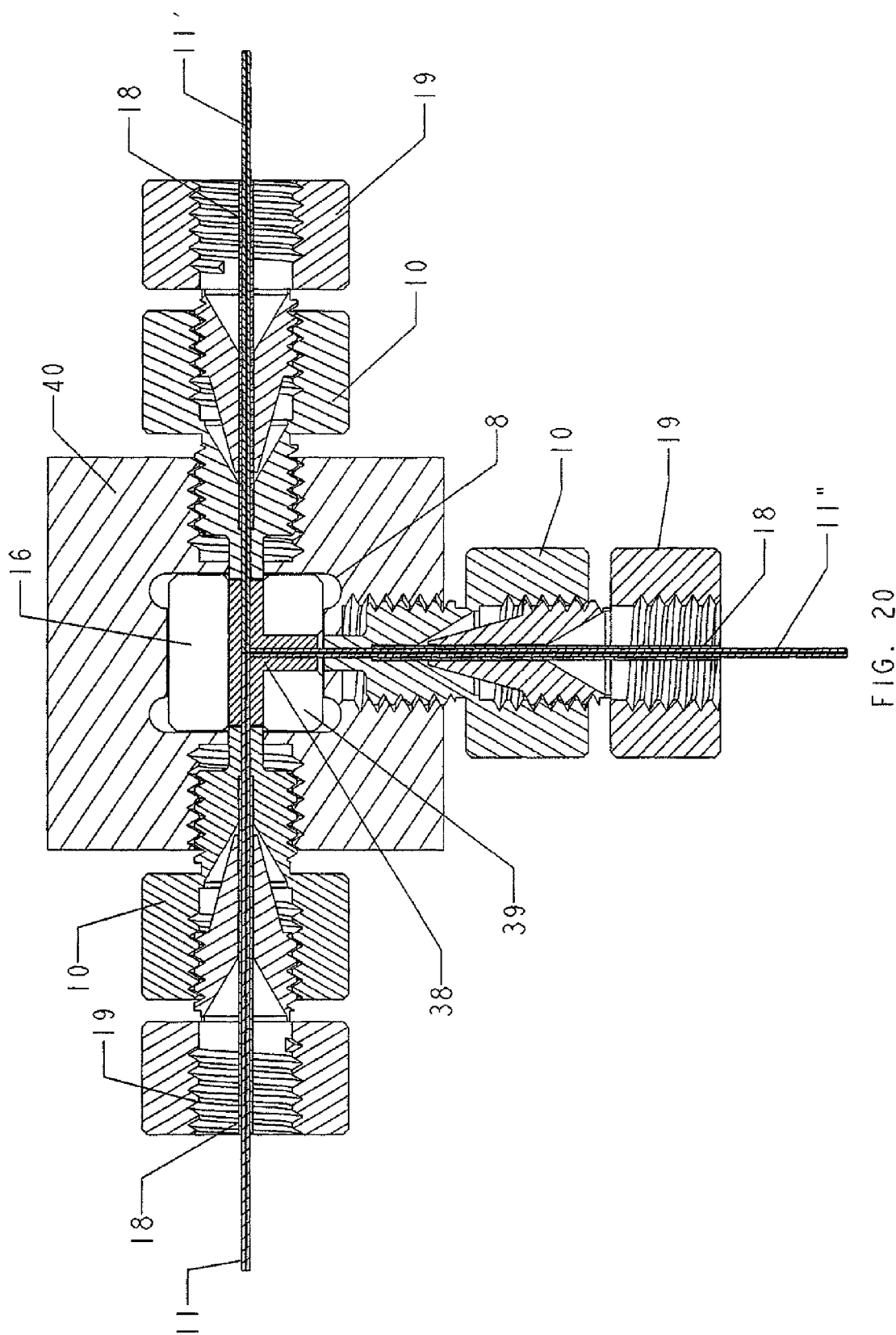
FIG. 20 is an sectional view of the union of FIG. 18b, as viewed through sight line 20-20.

A sectional view 20-20 of the union of FIG. 18b, as assembled, is illustrated in FIG. 20. This view also illustrates the use of polymeric sleeves 18 as aids in firmly holding small diameter tubing sections 11, 11' and 11", as previously discussed.

Turning now to the figures, FIG. 1 illustrates the union 1, comprised of a union body 4 which has been inserted into a recess 8 of housing 6 to form a cartridge-in-holder assembly. An elastomeric core 2 is inserted into the bore 5 of union body 4, and extends into the bore 7 of housing 6. Compression nuts 10 have been threaded into housing 6 to bear upon the ends of the core. Two segments of tubing 11, 11' have been inserted through bores in nuts 10, through bore 7 of housing 6 and into the bore 3 of elastomeric core 2 and meet within elastomeric core 2 at about the midpoint of the union body. Further tightening of the compression nuts 10 will impart an axial compression on elastomeric core 2 which, since prevented from expanding radially outwards by the bore 5 in union body 4, will compress radially inwards and against the segments of tubing to seal them. The quality of the contact between the two segments of tubing can be observed through window cut outs 9.

Figure 2:
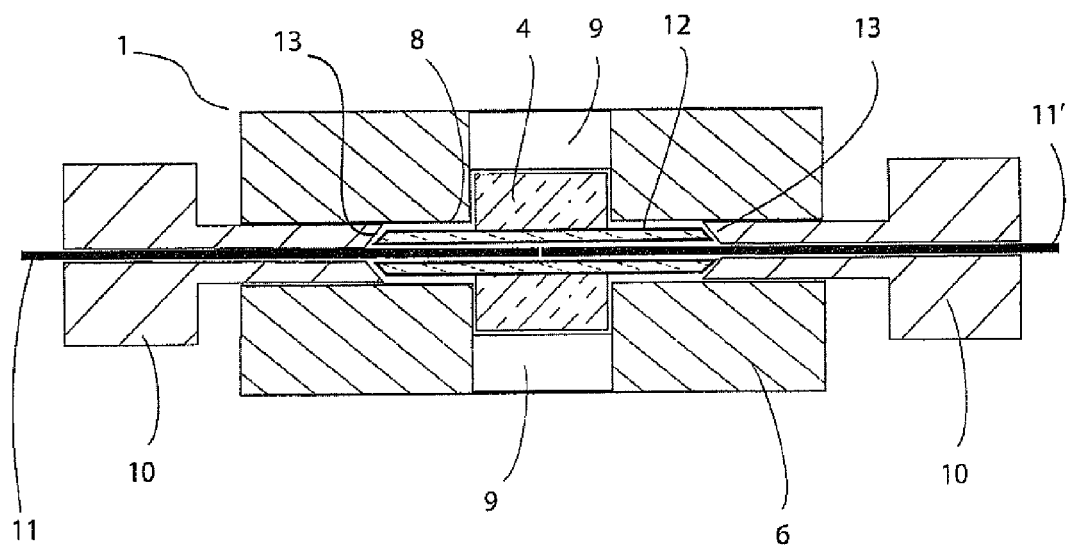
FIG. 2 illustrates an embodiment of the invention in which the ends of the elastomeric core of the union body and the ends of the tightening nuts have mating compression tapers to generate frusto-conical compression about the tubes to be joined.
Figure 3:
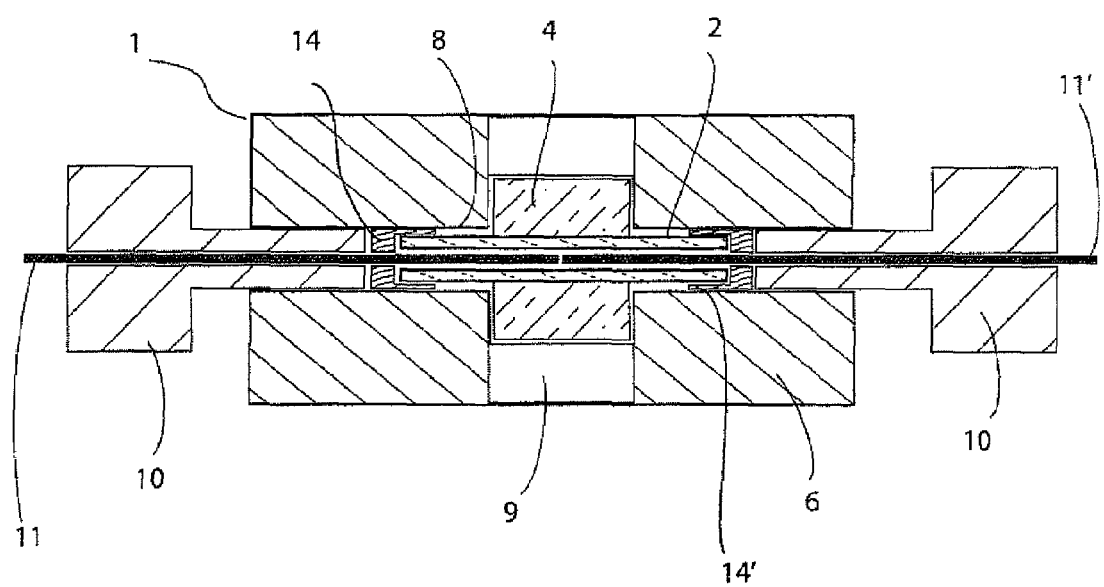
FIG. 3 illustrates the embodiment of FIG. 1, in which ferrules having a flat, cupped design (separate from the nuts) are utilized to bear against the core. This reduces the effects of rotational motion imparted by turning the nuts and increases containment of the core during compression.

In a further improvement, an elastomeric core having tapered ends 12 is used, and the ends of the nuts which contact the core to compress it are provided with matching tapers 13, as shown in FIG. 2. In a further embodiment, the ends of the core which are contacted by the tightening nuts can be provided with ferrules (14, 14') as shown in FIG. 3.

FIG. 4a is an exploded view of union 1, which is comprised of a union body 4 with elastomeric core 16, a union housing 6 having a recess 8 for insertion of the union body and bore with internal threads to mate with the threads on compression nuts 10. The union housing also is provided with a window cut-out 9. Also shown are flat-ended ferrules 15, 15'. FIG. 4b illustrates the use of the union of FIG. 4a to join tubing sections 11 and 11'. FIG. 4c is an cross-sectional view of FIG. 4b.

When the elastomeric core is inserted into the union body, friction alone may be sufficient to hold it in place. Where friction alone is not sufficient, however, the two can be bonded together with the use of an adhesive or gel, preferably an optically clear adhesive, epoxy, or cured gel 17, as shown in FIG. 5a (elastomeric core 2 extending outwardly from union body 4), FIG. 5b (elastomeric core 16 flush with union body) and FIG. 6 (elastomeric core 12 having tapered ends). FIG. 5c is an isometric view of the union body of FIG. 5b.

FIG. 7 is a cross-sectional view of a union similar to that of FIG. 4c, except that polymeric tubing sleeves 18 have been brought over the ends of the tubing sections 11, 11', passing into bores 52 in the distal ends of the primary compression nuts, and secondary compression nuts 19 with integral tapered ferrules have been screwed into the complementary internal taper of the primary compression nuts, over the added polymeric tubing sleeves 18 and tightened to provide further holding power on the tubing sections.

As shown in FIG. 8a, a union body 20 of the invention can be configured with a linear array of multiple bores and cores (not shown), and directly fitted with primary compression nuts 10 and secondary compression nuts 19, to provide a plurality of unions in a single unit. This embodiment is a linear array of that fully described by FIGS. 22a-d herein. The union body 20 is configured for use without a housing. Preferably the union body 20 is formed of a transparent material, so that the interior connections can be observed without the need for a window cut out. The union body 20 is shown with tube sections 11 and 11' in place. A polymeric sleeve 18 can be seen over tube section 11.

FIG. 8b is an end view of the union body of FIG. 8a, and FIG. 8c is a top view of the union body of FIG. 8a.

Figure 8E:
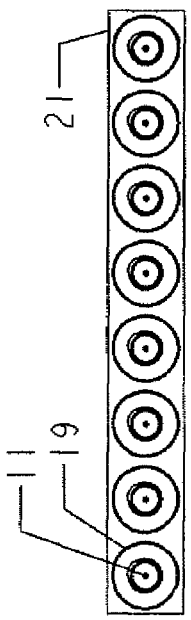
FIG. 8e is a side view of the union housing of FIG. 8d.
Figure 8G:
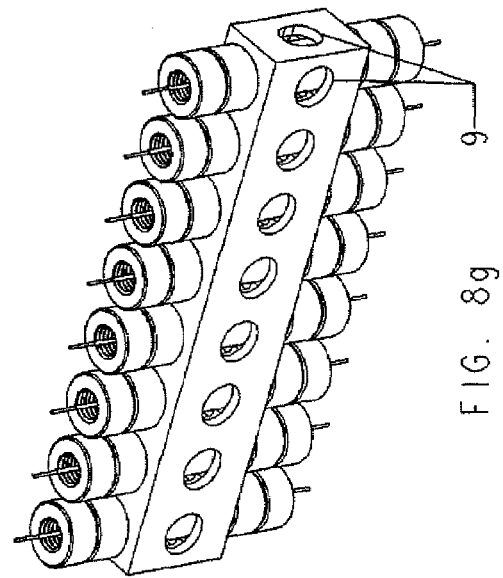
FIG. 8g illustrates the union body of FIG. 8a, with window cut outs added.
Figure 8D:
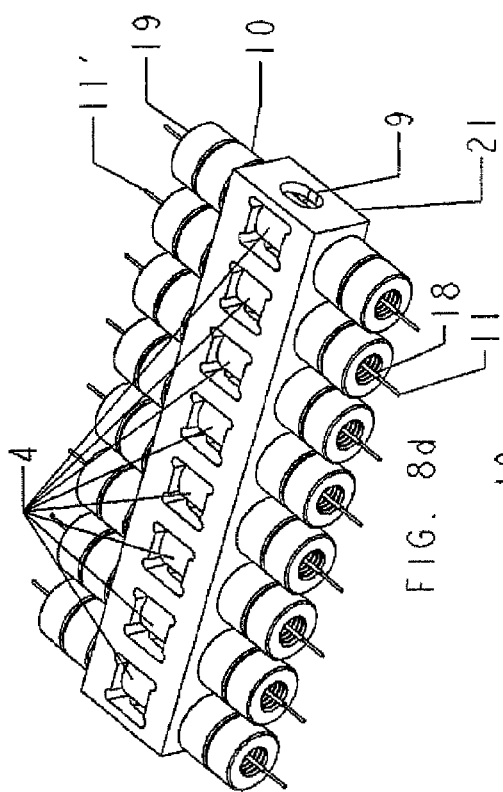
FIG. 8d illustrates a composite integral union housing having a linear array of multiple individual bores (not shown), primary compression nuts and secondary compression nuts, and a linear array of recesses with union bodies inserted as cartridge inserts.

FIG. 8d illustrates a configuration analogous to that of FIG. 8a, except that this is a housing-based embodiment, wherein the housing 21 comprises a linear array of multiple individual bores (not shown) leading into recesses 8. Union bodies 4 are inserted as cartridges through recesses 8 in the housing 21. The union bodies themselves are illustrated in FIG. 5c. In FIGS. 8d and 8g, window cut-outs 9 can be seen.

Figure 8F:
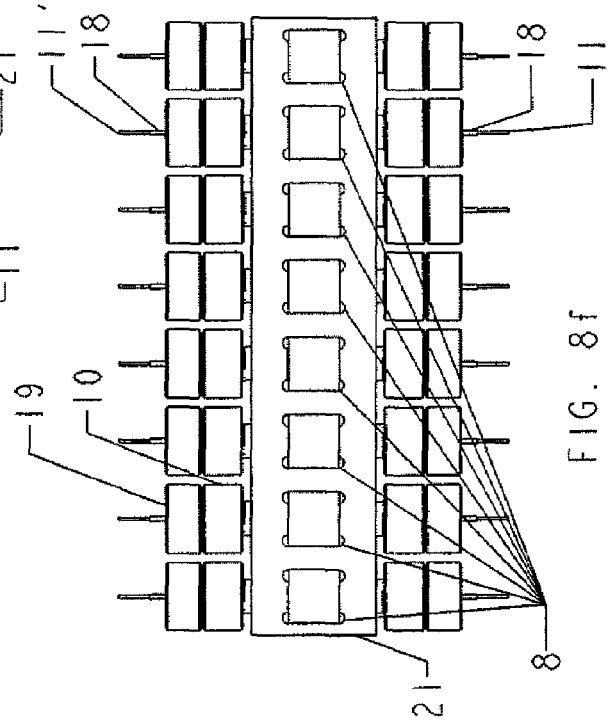
FIG. 8f is a top view of the union housing of FIG. 8d

FIG. 8e is an end view of the union of FIG. 8d, and FIG. 8f is a top view of the union of FIG. 8d. FIG. 8g is a view of the bottom of the union of FIG. 8d, wherein window cut-outs 9 for observing the connections in each union body can be seen.

In yet a further embodiment, a union body 22 having a plurality of bores 5 with elastomer cores 16, shown in FIG. 9a can be inserted into a housing 23, shown in FIG. 9b, configured to receive it and having a complementary number of bores 7. Tightening elements for this embodiment may be provided as a complementary number of compression nuts on plate 24, as shown in FIG. 9c, Although only one plate is illustrated, two such plates are used, one on each side of the housing. The assembly of union body, housing and plate with compression elements (compression plate) are held together with clamp 25, as illustrated in FIG. 9d. The holding power of the compressed core against the tubes may be supplemented through the use of secondary compression nuts 19, as previously discussed and as shown in FIGS. 9e and 7. The resulting union is illustrated in top view in FIG. 10a and in isometric view in FIG. 10b. The primary compression elements of FIGS. 10a and 10b cannot be seen, as they are hidden from view by the secondary compression nuts 19.

Figure 11A:
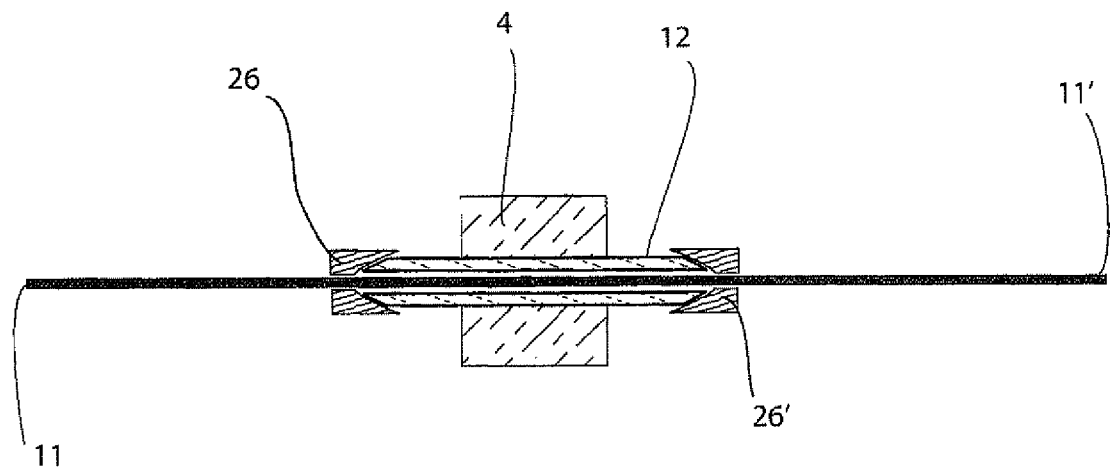
FIG. 11a illustrates a union body before compression, with ferrules in place over the ends of the elastomeric core. A clearance can be seen between the tubing segments and the internal walls of the core. The union housing and tightening nuts have been omitted for clarity.
Figure 11B:
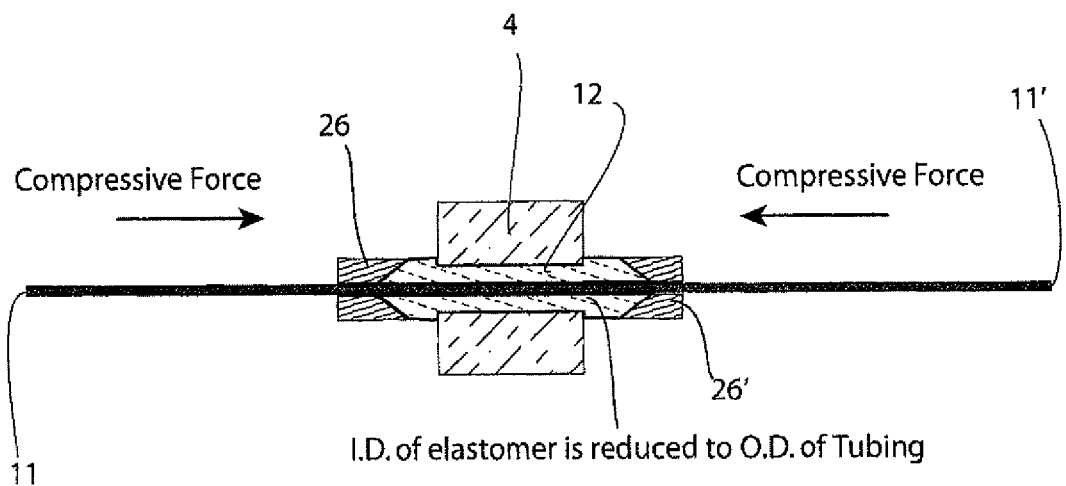
FIG. 11b illustrates the union body of FIG. 11a, but with the end ferrules pushed towards each other to axially compress the core. The elastomeric core has been deformed, and the ID has been reduced to make direct contact with the ODs of the two segments of tubing.

The mode of operation of the union can be seen by comparing FIG. 11a to FIG. 11b. FIG. 11a illustrates a core with tubing sections 11, 11' inserted prior to the tightening of the compression nuts (not shown) against the ferrules 26, 26' (the ferrules are illustrated with internal female tapers). A clearance can be seen between the tubing segments 11,11' and the inside walls of the core 12. In FIG. 11b, the nuts have been tightened against the ferrules, causing the portion of the core within the union body to expand radially inwardly against the tubing elements (11, 11') to sealingly engage them.

Figure 12A:
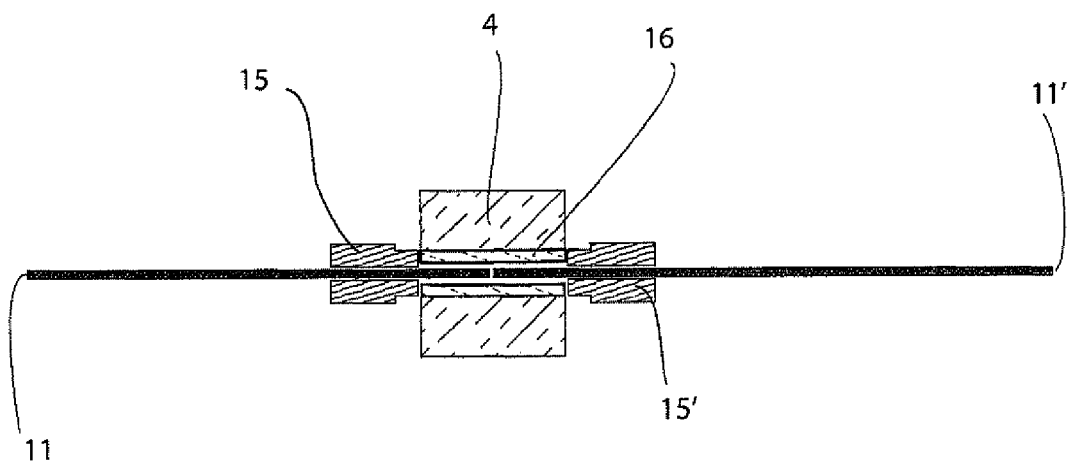
FIG. 12a illustrates a union body similar to that of FIG. 11a, before compression, except that the ends of the elastomeric core are flush with the ends of the bore of the union body, and ferrules having a flat ended cylindrical protrusion having an OD smaller than the ID of the union body bore are used.
Figure 12B:
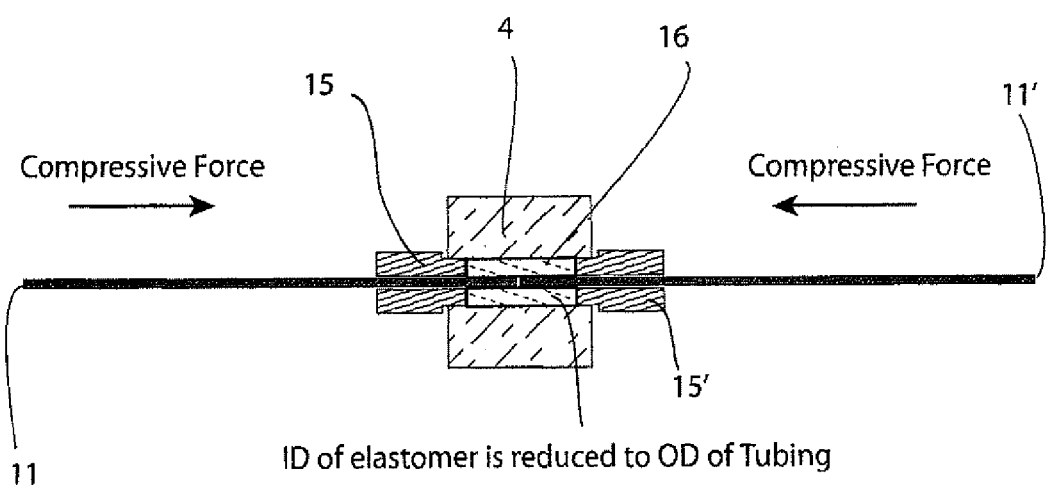
FIG. 12b illustrates the union body of FIG. 12a, with the primary nuts tightened (not shown) to compress the elastomeric core and seal the tubing segments.

FIGS. 12a and 12b illustrate the same mode of operation as is shown in FIGS. 11a and 11b, except that the elastomeric core 16 is shown initially flush with the union body, ferrules 15, 15' having flat ends which fit into the bore of the union body are shown. When compressed, the ferrules countersink into the bore of the union body.

Figure 13:
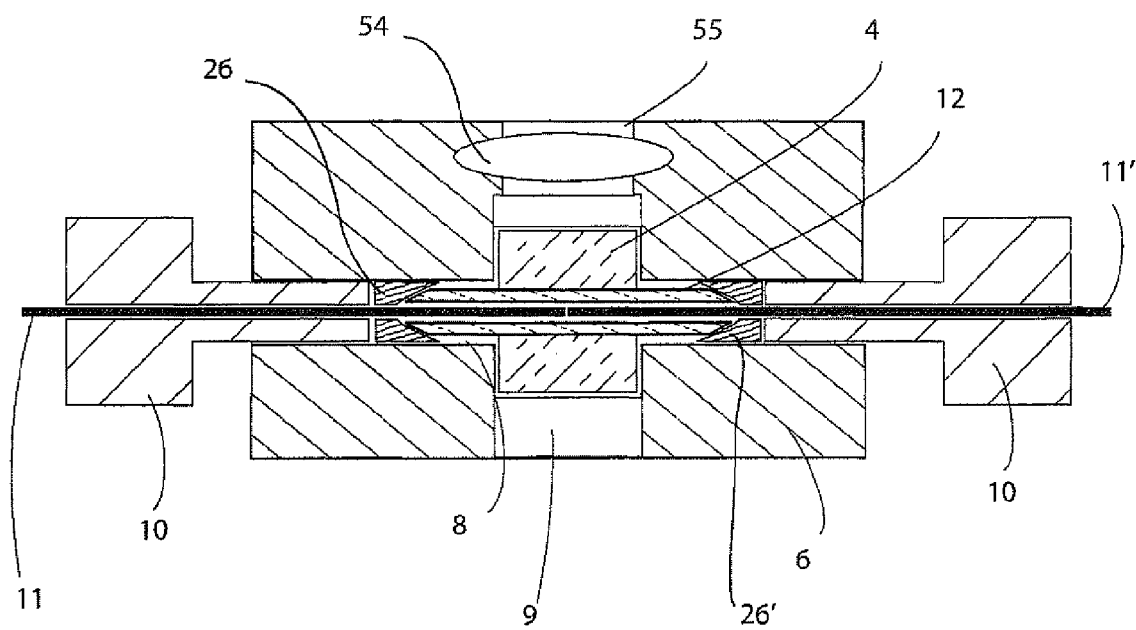
FIG. 13 illustrates an embodiment of the invention in which a magnifying lens is placed within the union housing to provide a magnified view of the tube sections within the union body.

FIG. 13 illustrates a union having a union body and union housing, similar to that of FIG. 2 except that separate ferrules 26, having internal female tapers are used and the housing in provided with a cut-out 55 for a lens, and magnification lens 54 is installed in that cut-out.

FIG. 21a is a cross-sectional view of the secondary compression nuts 19, having integral tapered ferrule 42, external thread 43, internal thread 44, internal taper 49 and bore 51 for passage of a tubing section 11, 11' etc. and polymer sleeves 18. Internal taper 49 can be used to accommodate additional secondary compression nuts, as $3^{rd}$ or $4^{th}$ compression elements to provide even greater hold on the tubing sections than that achieved using the primary and secondary compression nuts, as heretofore described, if desired. FIG. 21b is an isometric view of the secondary compression nut of FIG. 21a. FIG. 21c is a cross-sectional view of a primary compression nut 10 having internal thread 46, flat ended cylindrical protrusion 47, internal taper 48, bore 50 for passage of a tubing segment 11, 11' etc. and expanded bore 52 to accept a polymeric sleeve, as hereinbefore discussed. FIG. 21d is an isometric view of the primary compression nut of FIG. 21c, and FIG. 21e is a cross-sectional view of a secondary compression nut 19 mated with a primary compression nut 10.

EXAMPLES

Example 1

Union Body with Housing

A union body was fabricated from cut lengths of material. The body was fabricated from cylindrical glass tubing, having an OD of 0.290" and an ID of 0.063" which was cut and polished to a length of 0.20". The core was fabricated from cylindrical FEP tubing, having an OD of 0.062" and an ID of 0.016", cut to a length of 0.40". The core was etched in FluoroEtch solution (sodium in naphthalene) for a period of 1 minute, and then rinsed with distilled water. The core was placed inside the union body and the two were bonded together using Norland Optical Adhesive 83H (a methacrylate based UV curable photopolymer adhesive), following standard manufacturer protocols for UV exposure and polymer curing. Typically the assembly was exposed to UV light from a low wattage UV lamp for 30-60 minutes, and allowed to cure overnight in an oven at approx. 100° C. The union body had the geometry shown in FIG. 5a.

After curing, the union body was placed inside a stainless steel housing, having the geometry of a thick ring. The ring ID was 0.675" (OD of 0.920"), a sufficient diameter to permit the insertion of the union body into the center of the ring. Two threaded holes were machined 180° apart on the perimeter of the ring, perpendicular to the ring's main bore. These threaded holes accepted standard fingertight nuts fabricated from PEEK®. Prior to screwing in the nuts, each end of the core was fitted with a PEEK ferrule having the geometry shown in FIG. 3. Each ferrule had an OD of 0.150", a through bore of 0.025", and a counterbore of 0.0625" for a depth of 0.080". The counter-bore of each ferrule faced the center of the union body, with each end of the core inserted into its respective counterbore. The result of this assembly is the endcapping of the exposed core by the ferrules. The nuts were then screwed into the union body, but not far enough to compress the core. Two pieces of 0.0145" OD by 0.002" ID polyimide coated fused-silica tubing were fed into opposite ends of the core and pushed into position so that their facing ends met and touched in the center of the assembly. The nuts were then tightened to compress the core sufficiently to reduce the ID of the core and to hold the two pieces of tubing in place.

The connection was pressure tested by fitting the free end of the first tube to a high-pressure chromatographic pump (Agilent Inc., model 1100) set to deliver a mixture of water and acetonitrile at a concentration of 5%. The other end was fitted to a 100 μm ID×25 mm reverse phase chromatographic column (New Objective Inc.) to generate sufficient back pressure to pressure test the union. The flow rate of the pump was increased from zero, and adjusted so that the pressure generated by the pump was between 70 and 140 bar (approx. 1000 to 1500 psi). The union held the pressure for more than approx. 10 minutes and no leaks were apparent. The flow rate was then increased until the pressure was 170 bar (2500 psi) and no leaks were apparent.

Example 2

Opto-Electronic Detection of Union

Figure 14:
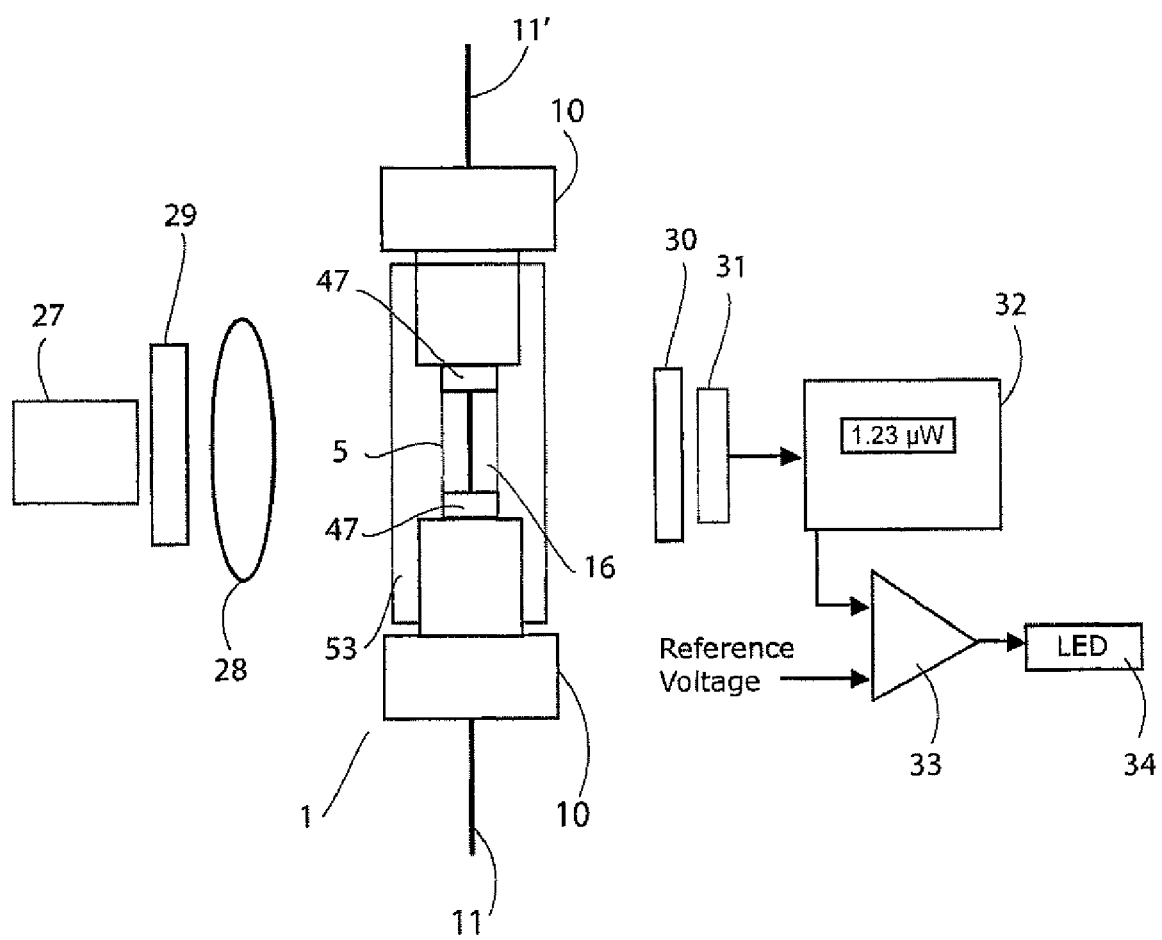
FIG. 14 illustrates an opto-electronic detection system for monitoring the quality of the connection between tubing or optical fiber sections being connected by the union of the invention.

As shown in FIG. 14, light from a laser diode 27 (670 nm, 4 mW) was passed though a focusing lens 28 and an optical density filter 29 (OD 3) yielding an elliptically focused beam having the approximate dimensions of 1.0×0.4 mm at the focal plane of the lens. A union housing body 53 (without the housing as in FIG. 22), having a core fabricated from 0.016" I.D.×0.062" O.D. FEP tubing, and a union housing body made from clear, square polymethylmethacrylate (PMMA) polymer having a cylindrical bore 0.063" I.D.×0.150" long at its center. Since this was a non-housing embodiment, the flat ended compression nuts 10 threaded directly into the clear union housing-body. These fittings had a terminal OD of 0.062" and could directly compress the core material by extending into the 0.063" bore of the union body. The union body was placed in this focal plane of the lens, with the long axis of the union parallel and coincident to the 1 mm axis of the beam. A photodiode detector 31, with a 670 nm bandpass filter 30, was placed opposite the beam. This photodiode produced a small electrical current which is proportional to the amount of light hitting the surface of the photodiode. This electrical current was collected by an amplification circuit (well known to those skilled in the art of electronics), converting the current into a voltage. The output of this circuit was a voltage that is proportional to the amount of light on the photodiode. This voltage was then fed to a comparator circuit 33, comparing the output voltage to a threshold value, determining whether the output voltage was less than, greater than, or equal to the threshold value. This comparator circuit may be based on either analog electronics (as in this example) or digital electronics, in which the comparison is made by a microprocessor by converting the analog output of the photodiode to a digital value.

Thus the union body was between the laser and photodiode and positioned such that the placement of tubing (or fiber) in the union affected the amount of light transmitted through the union to the detector. Furthermore the distance between the two pieces of tubing (or fiber) affected the amount of light transmitted through the assembly. The apparatus is shown in FIG. 14.

Figure 15:
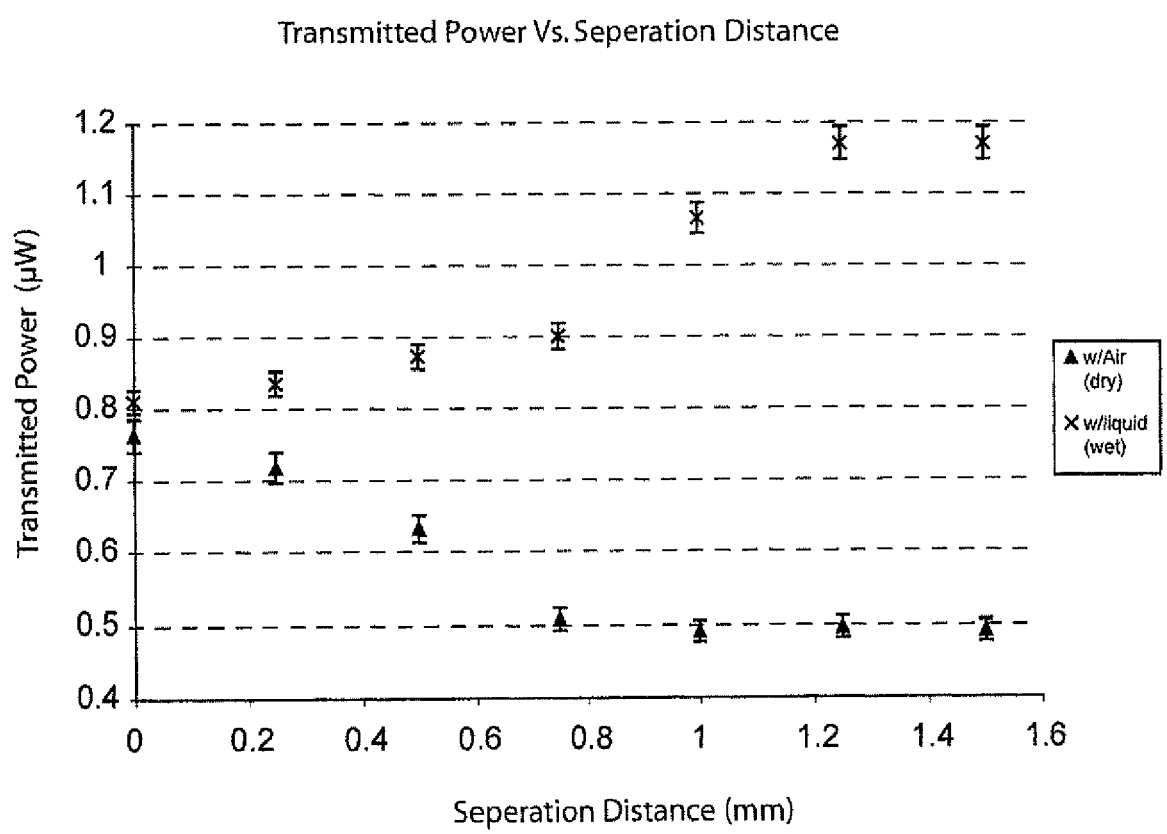
FIG. 15 is a graphical representation of the results obtained when measuring the optical transmission through the union body at a variety of separation distances between two pieces of fused silica tubing, using the opto-electronic detection system of FIG. 14.

The optical transmission through the union assembly was measured at a variety of separation distances between two pieces of fused silica tubing (360 μm O.D.×75 um I.D.). This was done first with the union and associated tubing dry (air filled). The assembly was then filled with an aqueous liquid (50% acetonitrile, 0.1% formic acid) and the measurements were repeated. For each measurement the separation between the two pieces of tubing was directly measured with a video microscope system (not shown in the apparatus drawing). The intensity measurements were made when the fittings were tightened, and the core was compressed. Such compression yielded the best quality measurement, since the optical clarity of the assembly and subsequent transmission was both repeatable and maximal. The results of this measurement are shown in FIG. 15, which shows the data points together with error bars.

The surprising result of this measurement is that not only can one distinguish a "good" connection (in which the two pieces of tubing are close together) from a "poor" connection (in which the two pieces are far apart), one can use both the absolute value of the transmission in combination with transmission measurements made at different tubing separations to distinguish connections made in air from one made in a liquid. Thus the presence of air in a fluid connection may be readily determined.

The voltage output of the amplification circuit 32 was fed to a comparator circuit based on an LM311 integrated circuit (National Semiconductor Corporation) having an "open collector" output. The LM311 comparator circuit compares the value of the (amplifier output) voltage to a reference voltage, and switches its output from an "off" state to an "on" state when the levels cross value. The comparator output fed a pull-up resistor and green light-emitting diode (LED) 34 configured such that the LED would turn on when the output of the amplifier went above the reference voltage. The reference voltage was provided by a variable resistor (potentiometer) voltage divider and voltage follower circuit supplying the LM311. Thus when the assembly was dry, a good connection (here defined as less than 0.1 mm separation distance between pieces of tubing) was indicated when the LED was on, When liquid filled, a good connection was indicated when the LED was off.

This embodiment utilized discrete optical components and electronic circuitry. The entire assembly may be miniaturized and made compact by combining the optical elements and electronics through the micro-lithographic fabrication of electronics and circuit board manufacturing, well known to those skilled in the art. Such circuits as the light source (either laser diode or light-emitting diode) and photodiode detector may be placed directly on a flexible polyimide based circuit board containing all necessary electronics to enable the measurement. This electronics package can then be integrated directly with and into the union body, yielding a coupling union that is self-diagnostic, determining and indicating whether a good connection is present.

Such an assembly may be further enhanced by enabling the electronic circuit to be in either wired or wireless communication with a centralized data collection resource or network, such as that provided by internet communication protocols, known to those skilled in the art. Thus said connection quality may be monitored through remote means.

Example 3

Coupling of Optical Fibers

The unique properties of the invention permit high efficiency coupling of light from one optical fiber to another. When the elastomer core is compressed, its I.D. reduces to the O.D. of the fibers being connected. Furthermore, since the core is one continuous ID, the coaxial alignment of the two fibers will be excellent, and essentially self-aligning.

Figure 16:
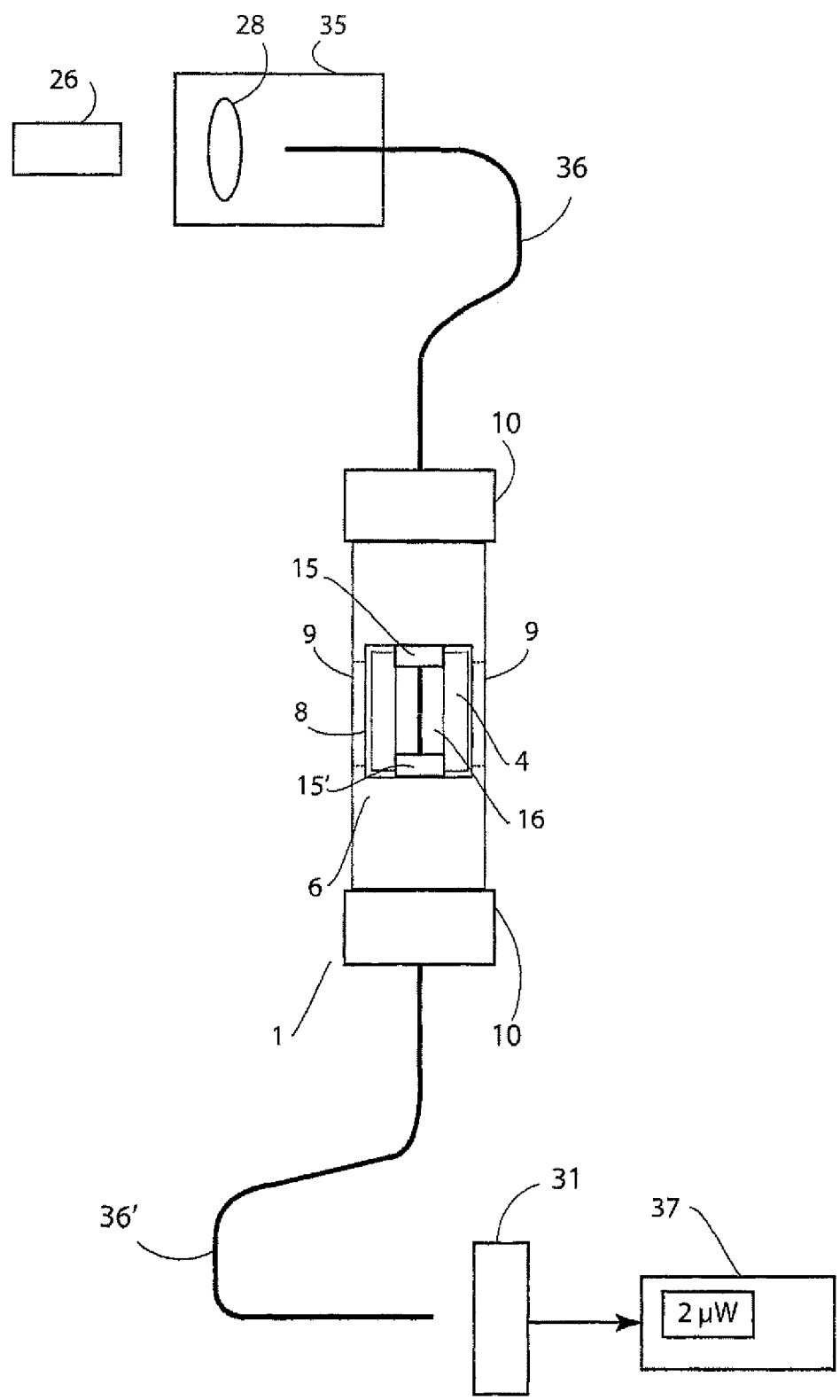
FIG. 16. illustrates the union being used to connect two sections of optical fiber.

In this example a union of the cartridge design (as in FIGS. 4a-c) was used to connect two pieces of small core diameter single mode optical fiber. The apparatus is shown in FIG. 16.

Light from a laser diode 26 (670 nm, 4 mW) was launched into a first single mode optical fiber 36 (3.2 μm O.D. core, 125 μm O.D. cladding, 250 μm O.D. polymer jacket, 488 nm design wavelength, cleaved at both ends to 20 cm length) using a fiber coupling stage with a ball lens (Newport Corporation). The free end of fiber 36 was inserted into the union assembly 1, having a 0.010" I.D.×0.062" O.D.×0.280" long FEP elastomer core 16. The cartridge union body shell 4 was fabricated from glass tubing (0.063" I.D.×0.290" O.D.× 0.285" long). A second fiber 36', identical to the first, was inserted into the opposite end of the union 4, having window cut out 9, and pressed into light contact with the first fiber. The primary compression nuts 10 were tightened so that the elastomer core 16 was compressed by the flat end 47 of the fitting on each end protruding into the bore of the glass shell. This compression reduced the elastomer ID to the OD of the optical fiber over its entire length. The transmission ratio through the connection was determined by measuring the amount of light emitted by the second fiber 36' onto a photodiode 31 equipped optical power meter 37. Immediately after this measurement the first fiber 36 was removed from the union and the amount of light emitted by it was similarly recorded. The transmission efficiency is the ratio of the power emitter by the second fiber 36' to the amount delivered by first fiber 36. This measurement was repeated a number of times with different sections of fiber.

A second set of measurements was made with the addition of a refractive index coupling oil (Nd=1.540) between the two pieces of optical fiber. Said liquid was introduced into the elastomer core before fiber 36' was inserted into the assembly. The light tight seal of the connection enables the efficient use of liquid based coupling media to improve optical efficiency. Both sets of measurements are shown in table 1. Even though the core diameter is less than 4 μm, the coupling efficiency averaged 46% and can be greater than 70%, indicating excellent alignment between the two fibers.

It was further noted that the amount of scattered light visible through the window cut outs 9 was inversely proportional to the coupling efficiency. Thus the quality of the fiber optic connection could be rapidly monitored and determined by the intensity of light detected through the window cut outs by either visual or opto-electronic means.

TABLE 1

Coupling Efficiency measurements in air and oil (Nd = 1.540).

| Launch Power from Fiber #1 (μW) | Coupled Power from Fiber #2 (μW) | Ratio |
|---|---|---|
| in Air: | | |
| 105 | 55 | 52% |
| 105 | 26 | 25% |
| 105 | 65 | 62% |
| 80 | 45 | 56% |
| 80 | 10 | 13% |
| 80 | 35 | 44% |
| | Average | 42% |
| In Oil | | |
| 98 | 75 | 77% |
| 130 | 84 | 65% |
| 95 | 23 | 24% |
| 95 | 35 | 37% |
| 95 | 40 | 42% |
| | Average | 49% |

Example 4

Pressure Test with Polymer Union Body

This experiment was conducted with an apparatus similar to that illustrated in FIGS. 4*a-c*, but provided with both Primary (tightening) nuts (10) and Secondary (holding) nuts (24) with sleeves (18) such as those shown in FIG. 7, used to connect two pieces of 360 micron diameter polyimide coated fused silica capillary tubing. The union housing (4) was fabricated from either borosilicate glass or cast and machined polymer PMMA, having a bore ID of 0.063". The elastomer core was made from a cut section of extruded FEP tubing having an OD of 0.062" and a 0.016" bore ID. The union housing (6) was fabricated from machined aluminum. The primary (10) and secondary (19) compression nuts were machined from PEEK polymer. The polymer sleeve (18) was made from extruded PEEK tubing having an OD of 0.025" and a 0.018" bore ID. The two lengths of tubing being connected were approx. 30-40 cm long. The union was assembled with the two lengths of tubing joined at the center of the union core. The primary and secondary nuts (when used) were all tightened by hand, without the use of additional tools. There were two parts to this test:

First: An initial pressure testing of the sealing functionality of the device. For this test, only the Primary Nuts were engaged thus forming the primary liquid tight seal.

Second: A second pressure test with the locking portion (Secondary nuts) of the device engaged. For this test, both the primary nuts and secondary nuts were engaged.

The test assembly consisted of an Agilent 1100 series HPLC system which uses a Model G1312A Binary Pump connected to the first length of tubing. A 100 micron ID, C18 packed nanobore column was connected to the second length of tubing to create back pressure.

For each run of the test, the union was flow tested with HPLC grade water to ensure there was no blockage. Then the fluid pressure was increased by increasing the flow rate of the pump until the device exhibited signs of leakage and or pressure loss. Each run of the device used a new elastomeric core 16 (FEP), as it was assumed that the used core had been physically compromised. Tests one through four utilized a borosilicate glass union body which was prone to rupture. Tests six through ten utilized a cast polymer union body, which was far less brittle and exhibited no rupture.

The table below lists the data for the first test (primary (tightening) nuts engaged only):

TABLE 2

Results of the pressure tests with primary holding nuts only

| TRIAL [#] | PRESSURE MAX [BAR (PSI)] | EJECT/RUPTURE [E/R] |
|---|---|---|
| 1 | 127 (1842) | R |
| 2 | 150 (2176) | R |
| 3 | 280 (4061) | R |
| 4 | 140 (2031) | R |
| 5 | 230 (3336) | E |
| 6 | 180 (2611) | E |
| 7 | 155 (2250) | E |
| 8 | 230 (3336) | E |
| 9 | 235 (3408) | E |
| 10 | 225 (3263) | E |

Three additional tests were performed with the secondary (holding) nuts engaged when using the polymer PMMA housing. All three tests were successful in that a maximum holding pressure of the assembly was greater than the maximum operating pressure (400 bar/5802 psi) of the pump.

| | Index to drawings |
|---|---|
| 1 | union |
| 2 | elastomeric core |
| 3 | bore in elastomeric core |
| 4 | free floating union body |
| 5 | bore in union body |
| 6 | union housing |
| 7 | bore in union housing |
| 8 | recess (slot) in union housing |
| 9 | window cut-out in union housing |
| 10 | compression element (tightening nut) |
| 11, 11', 11" | tube sections |
| 12 | elastomeric core with tapered ends |
| 13 | compression taper on compression element |
| 14, 14' | cupped ferrules with counterbore to accept core |
| 15, 15' | ferrules having a square ended, flat protrusion |
| 16 | Elastomeric core having ends which are flush with the ends of the union body bore |
| 17 | optically clear adhesive or gel |
| 18 | polymeric tubing sleeves |
| 19 | secondary compression nut with integral tapered ferrule |
| 20 | union body with array of elastomeric cores |
| 21 | union housing with linear array of multiple individual bores and multiple recesses for insertion of union body cartridges |
| 22 | union body with array of elastomeric cores, configured as cartridge insert for insertion into housing with multiple bores |
| 23 | housing with multiple bores configured for insertion of cartridge insert with array of elastomeric cores |
| 24 | plate with series of compression elements |
| 25 | clamp |
| 26 | ferrule with internal female taper |
| 27 | laser diode |
| 28 | focusing lens |

-continued

| | Index to drawings |
|---|---|
| 29 | optical density filter |
| 30 | bandpass filter matched to laser diode wavelength |
| 31 | photodiode detector |
| 32 | amplification circuit |
| 33 | comparator circuit |
| 34 | opto-electronic indicator (light emitting diode) |
| 35 | fiber optic coupler |
| 36, 36' | optic fiber |
| 37 | optical power meter |
| 38 | "T" shaped elastomeric core |
| 39 | two-part union body for "T" shaped elastomeric core |
| 40 | multi-port union housing having orthogonal ports |
| 41 | molded union body with formed-in-place "T" shaped elastomeric core |
| 42 | integral tapered ferrule |
| 43 | external thread on secondary compression nut |
| 44 | internal thread on secondary compression nut |
| 45 | external thread on primary compression nut (tightening nut) |
| 46 | internal thread on primary compression nut (tightening nut) |
| 47 | square ended flat protrusion on primary compression nut |
| 48 | Internal taper on primary compression nut |
| 49 | internal taper on secondary compression nut |
| 50 | bore in primary compression nut to accept tube |
| 51 | bore in secondary compression nut to accept polymer sleeve |
| 52 | bore in primary nut to accept polymer sleeve |
| 53 | union housing with integral union body |
| 54 | magnification lens |
| 55 | cut out for magnification lens |
| 56 | internal thread on combined union housing-body |

We claim:

1. A union for coupling two or more segments of tubing or optical fiber, comprising
   a) an elastomeric core having one or more linear or branched tubular sections, each having an internal bore, which, when more than one tubular section is present, is in fluid or optical communication with the internal bores of the other tubular sections,
   b) a union body having a through bore for each of said one or more tubular sections, which girdles said tubular section or sections, the size and shape of said through bore or bores of said union body being complementary to the size and shape of the tubular core section girdled by each and the dimensions of said through bore or bores of said union body approximating but exceeding the outside diameter of the corresponding tubular core section, so as to substantially prevent outward radial expansion of said tubular core section or sections,
   c) a housing having at least one through bore with an inlet and outlet, said at least one bore being interrupted by a recess in said housing having a size and dimensions sufficient to accommodate the removable insertion of said union body, to permit said union body to float freely within said housing to align said elastomeric core or cores of said union body with the through bore or bores of said housing upon insertion of segments of tubing or optical fiber through said through bore or bores of said housing and into said tubular sections within said union body,
   d) compression elements engagable with said housing to impart an axial compression upon said elastomeric core of said union body when the through bore or bores of said union body is or are aligned with said at least one through bore or bores of the housing,
   whereby upon insertion of segments of tubing or optical fiber having an outside diameter which approximates or is less than the internal diameter of said bore or bores of said section or sections of elastomeric cores into said bore or bores of said elastomeric core section or sections and axial compression of said elastomeric core section or sections by said compression elements in combination with the prevention of radial outward expansion of said elastomeric core section or sections by said bore or bores of said union body, an inward radial compression is imparted to said elastomeric core section or sections to sealingly engage said segments of said tubing or optical fiber.

2. The union of claim 1, wherein said compression elements are compression nuts.

3. The union of claim 2, wherein said compression nuts comprise mating primary compression nuts and secondary compression nuts.

4. The union of claim 3, wherein polymeric sleeves are disposed over at least a portion of said segments of tubing or optical fiber passing through the bores of said primary and secondary compression nuts.

5. The union of claim 3 or 4, wherein at least some of said compression nuts have integral ferrules.

6. The union of claim 2, wherein ferrules are disposed between said compression nuts and said elastomeric core section or sections.

7. The union of claim 2, wherein at least some of said compression nuts have integral ferrules.

8. The union of claim 1, wherein said union body is cylindrical.

9. The union of claim 1, wherein said portion or portions of said elastomeric core section or sections girdled by said through bore of said union body is adhesively bonded to said through bore of said union body.

10. The union of claim 1, wherein said union body comprises a linear array of through bores and elastomeric core sections within said through bores, and said housing comprises multiple through bores and is configured to accept said elastomeric core and align said multiple through bores with said through bores and elastomeric core sections of said union body.

11. The union of claim 10, wherein said union body comprises a plurality of linear arrays of through bores and elastomeric cores.

12. The union of claim 10 or 11, wherein said compression elements are a linear array of compression nuts on a plate configured to align with said through bores of said housing.

13. The union of claim 12, wherein said union body, housing and plate are held together with a clamp.

14. The union of claim 1, wherein said union body and elastomeric core are transparent.

15. The union of claim 1, wherein said housing includes at least one window cut-out through which at least a portion of said segments of tubing or optical fiber within said union body may be observed.

16. The union of claim 15, comprising a magnifying lens on or in said window cut-out.

17. The union of claim 15 further comprising opto-electronic detection apparatus for monitoring, through the window-opening, the coupling of tubing segments within said union housing.

18. The union of claim 17 further comprising an opto-electronic light source with necessary focusing lens or lenses; opto-electronic detector; detection, amplification and discrimination circuitry; and an electronic indicator, all or in part integrated into the body of the union housing.

19. Union of claim 18, wherein said light source and detector are positioned on opposite sides of the union elastomeric core.

20. Union of claim 18, wherein said light source is a light emitting diode, said opto-electronic detector is a photodiode, said opto-electronic indicator is a light emitting diode.

21. Union of claim 18, where said detection, amplification, and discrimination circuitry is comprised of analog electronic components.

22. Union of claim 18, where said detection, amplification, and discrimination circuitry is comprised of a mixture of analog and digital electronic components.

23. Union of claim 18, where said light source is a laser diode, said opto-electronic detector is a photodiode, said opto-electronic indicator is a light emitting diode.

24. The union of claim 1, wherein at least one of said tubing segments comprises a filter.

25. The union of claim 1, wherein said elastomeric core is fabricated from electrically conductive material.

26. The union of claim 1, wherein said union is configured as a "T", a cross, a star or a sphere having an elastomeric tubular core of said configuration.

27. The union of claim 26, wherein said compression nuts have ends which match said tapered ends of said elastomeric core.

28. The union of claim 1, wherein said elastomeric core has tapered ends.

29. A method of connecting at least two segments of tubing or optical fiber, which comprises connecting said segments with the union of claim 1.

30. The method of claim 29 wherein said two segments are segments of tubing, the elastomeric core is electrically conductive, a fluid is passed through said segments, said elastomeric core is connected to a source of electrical energy and an electrical charge is impressed upon said fluid.

* * * * *